US011162095B2

(12) United States Patent
Dutreix et al.

(10) Patent No.: US 11,162,095 B2
(45) Date of Patent: *Nov. 2, 2021

(54) USE OF A COMBINATION OF DBAIT MOLECULE AND PARP INHIBITORS TO TREAT CANCER

(71) Applicants: INSTITUT CURIE, Paris (FR); CENTRE NATIONAL DE LA RECHERCHE SCIENTIFIQUE, Paris (FR); ONXEO, Paris (FR); INSTITUT NATIONAL DE LA SANTE ET DE LA RECHERCHE MEDICALE, Paris (FR); UNIVERSITE PARIS-SUD 11, Orsay (FR)

(72) Inventors: Marie Dutreix, L'Hay-les-Roses (FR); Wael Jdey, Longjumeau (FR)

(73) Assignees: INSTITUT CURIE, Paris (FR); CENTRE NATIONAL DE LA RECHERCHE SCIENTIFIQUE, Paris (FR); ONXEO, Paris (FR); INSTITUT NATIONAL DE LA SANTE ET DE LA RECHERCHE MEDICALE, Paris (FR); UNIVERSITE PARIS-SUD 11, Orsay (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/790,788

(22) Filed: Feb. 14, 2020

(65) Prior Publication Data

US 2020/0172901 A1 Jun. 4, 2020

Related U.S. Application Data

(63) Continuation of application No. 15/746,806, filed as application No. PCT/EP2016/067479 on Jul. 22, 2016, now Pat. No. 10,563,197.

(30) Foreign Application Priority Data

Jul. 23, 2015 (EP) .................................... 15306201
Apr. 22, 2016 (EP) .................................... 16166674

(51) Int. Cl.
*A61K 48/00* (2006.01)
*C12N 15/11* (2006.01)
(Continued)

(52) U.S. Cl.
CPC .......... *C12N 15/111* (2013.01); *A61K 31/166* (2013.01); *A61K 31/4184* (2013.01);
(Continued)

(58) Field of Classification Search
CPC .............. C12N 2320/31; C12N 15/111; C12N 2310/13; A61K 31/166; A61K 31/711; A61P 35/00
See application file for complete search history.

(56) References Cited

U.S. PATENT DOCUMENTS 5,965,404 A 10/1999 Buschle et al.
6,420,176 B1 7/2002 Lisziewicz et al.
(Continued)

FOREIGN PATENT DOCUMENTS

EP 2 918 292 9/2015
WO WO 91/14696 10/1991
(Continued)

OTHER PUBLICATIONS

Croset, A. et al. "Inhibition of DNA damage repair by artificial activation of PARP with siDNA" *Nucleic Acids Research*, Jun. 12, 2013, pp. 7344-7355, vol. 41, No. 15, Supplemental Figures and Legends pp. 1-6.
(Continued)

*Primary Examiner* — Terra C Gibbs
(74) *Attorney, Agent, or Firm* — Saliwanchik, Lloyd & Eisenschenk

(57) ABSTRACT

The present invention relates to the combination of a PARP inhibitor with a Dbait molecule for treating cancer.

**16 Claims, 12 Drawing Sheets
(3 of 12 Drawing Sheet(s) Filed in Color)
Specification includes a Sequence Listing.**

(51) Int. Cl.
*C07H 21/02* (2006.01)
*C07H 21/04* (2006.01)
*A61K 31/4184* (2006.01)
*C12N 15/117* (2010.01)
*A61K 31/502* (2006.01)
*A61K 31/454* (2006.01)
*A61K 31/713* (2006.01)
*A61K 31/55* (2006.01)
*A61P 35/00* (2006.01)
*A61K 31/166* (2006.01)
*A61K 31/711* (2006.01)
*A61K 45/06* (2006.01)

(52) U.S. Cl.
CPC .......... *A61K 31/454* (2013.01); *A61K 31/502* (2013.01); *A61K 31/55* (2013.01); *A61K 31/711* (2013.01); *A61K 31/713* (2013.01); *A61K 45/06* (2013.01); *A61P 35/00* (2018.01); *C12N 15/117* (2013.01); *C12N 2310/13* (2013.01); *C12N 2320/31* (2013.01)

(56) References Cited

U.S. PATENT DOCUMENTS

| | | | |
|---|---|---|---|
| 7,476,729 | B2 | 1/2009 | Dutreix et al. |
| 7,595,302 | B2 | 9/2009 | Dutreix et al. |
| 7,635,722 | B1 | 12/2009 | Bachynsky et al. |
| 7,741,308 | B2 | 6/2010 | Dutreix et al. |
| 8,093,366 | B2 | 1/2012 | Dutreix et al. |
| 9,205,099 | B2 | 12/2015 | Sun et al. |
| 9,205,101 | B2 | 12/2015 | Dutreix et al. |
| 9,428,538 | B2 | 8/2016 | Sun et al. |
| 9,687,557 | B2 | 6/2017 | Sun et al. |
| 10,363,317 | B2 * | 7/2019 | Sun .............. A61K 31/713 |
| 10,765,758 | B2 * | 9/2020 | Sun .............. A61K 31/713 |
| 2007/0060499 | A1 | 3/2007 | Kosak |
| 2007/0111961 | A1 | 5/2007 | Dutreix et al. |
| 2009/0081237 | A1 | 3/2009 | D'Andrea et al. |
| 2012/0207856 | A1 | 8/2012 | Goel et al. |
| 2014/0051591 | A1 | 2/2014 | O'Donnell et al. |
| 2015/0335609 | A1 | 11/2015 | Balasubramanian et al. |
| 2017/0298089 | A1 | 10/2017 | Sun et al. |

FOREIGN PATENT DOCUMENTS

| | | |
|---|---|---|
| WO | WO 95/31541 | 11/1995 |
| WO | WO 95/33061 | 12/1995 |
| WO | WO 96/41606 | 12/1996 |
| WO | WO 97/25339 | 7/1997 |
| WO | WO 00/32815 | 6/2000 |
| WO | WO 2005/040378 | 5/2005 |
| WO | WO 2008/034866 | 3/2008 |
| WO | WO 2008/084087 | 7/2008 |
| WO | WO 2009/063998 | 5/2009 |
| WO | WO 2010/056403 | 5/2010 |
| WO | WO 2010/082821 | 7/2010 |
| WO | WO 2011/161075 | 12/2011 |
| WO | WO 2012/163814 | 12/2012 |
| WO | WO 2014/004884 | 1/2014 |
| WO | WO 2014/170441 | 10/2014 |

OTHER PUBLICATIONS

Jdey, W. et al. "Drug Driven Synthetic Lethality: bypassing tumor cell genetics with a combination of Dbait and PARP inhibitors" *Clinical Cancer Research*, retrieved from the Internet on Aug. 24, 2016: http://clinicancerres.aacrjournals.org/content/early/2016/08/24/1078-0432.CCR-16-1193.full-text.pdf.

Written Opinion in International Application No. PCT/EP2016/067479, dated Oct. 31, 2016, pp. 1-5.

Zhang, L. et al. "Targeting Ku protein for sensitizing of breast cancer cells to DNA-damage" *International Journal of Molecular Medicine*, 2004, pp. 153-159, vol. 14, XP-008084143.

Yoo, S. et al. "Characterization of the RNA Binding Properties of Ku Protein" *Biochemistry*, 1998, pp. 1336-1343, vol. 37, XP-002452541.

Chen, Q. et al. "Lipophilic siRNAs mediate efficient gene silencing in oligodendrocytes with direct CNS delivery" *Journal of Controlled Release*, 2010, pp. 227-232, vol. 144, XP-002601402.

Written Opinion in International Application No. PCT/EP2011/060280, dated Jul. 26, 2011, pp. 1-6.

Crooke, S. T. et al. "Pharmacokinetic Properties of Several Novel Oligonucleotide Analogs in mice" *The Journal of Pharmacology and Experimental Therapeutics*, 1996, pp. 923-937, vol. 277, No. 2.

Gamper, H. B. et al. "Facile preparation of nuclease resistant 3' modified oligodeoxynucleotides" *Nucleic Acids Research*, 1993, pp. 145-150, vol. 21, No. 1.

Solass, W. et al. "Therapeutic approach of human peritoneal carcinomatosis with Dbait in combination with capnoperitoneum: proof of concept" *Surgical Endoscopy*, 2012, pp. 847-852, vol. 26.

Quanz, M. et al. "Small-Molecule Drugs Mimicking DNA Damage: A New Strategy for Sensitizing Tumors to Radiotherapy" *Clinical Cancer Research*, 2009, pp. 1308-1316, vol. 15.

Written Opinion in International Application No. PCT/EP2012/059799, dated Sep. 12, 2012, pp. 1-7.

Devun, F. et al. "Preclinical study of the DNA repair inhibitor Dbait in combination with chemotherapy in colorectal cancer" *Journal of Gastroenterology*, 2012, pp. 266-275, vol. 47.

Quanz, M. et al. "Hyperactivation of DNA-PK by Double-Strand Break Mimicking Molecules Disorganizes DNA Damage Response" *PloS ONE*, Jul. 2009, pp. 1-11, vol. 4, Issue 7.

Storm, F. K. et al. "Hyperthermic Therapy for Human Neoplasms: Thermal Death Time" *Cancer*, Oct. 15, 1980, pp. 1849-1854, vol. 46, No. 8.

Papeo, G. et al. "PARP inhibitors in cancer therapy: an update" *Expert Opinion on Therapeutic Patents*, 2013, pp. 503-514, vol. 23, No. 4.

* cited by examiner

SEQUENCE LISTING

```
<160> NUMBER OF SEQ ID NOS: 22

<210> SEQ ID NO 1
<211> LENGTH: 32
<212> TYPE: DNA
<213> ORGANISM: artificial sequence
<220> FEATURE:
<223> OTHER INFORMATION: Dbait32

<400> SEQUENCE: 1
acgcacgggt gttgggtcgt tgttcggat ct                              32

<210> SEQ ID NO 2
<211> LENGTH: 32
<212> TYPE: DNA
```

```
<213> ORGANISM: artificial sequence
<220> FEATURE:
<223> OTHER INFORMATION: Dbait32Ha

<400> SEQUENCE: 2
cgtaggtctg tttggtggct ttgcagtggc ac                                   32

<210> SEQ ID NO 3
<211> LENGTH: 32
<212> TYPE: DNA
<213> ORGANISM: artificial sequence
<220> FEATURE:
<223> OTHER INFORMATION: Dbait32Hb

<400> SEQUENCE: 3
gctaggcttg tttgctgggt tgtaggcaca gc                                   32

<210> SEQ ID NO 4
<211> LENGTH: 32
<212> TYPE: DNA
<213> ORGANISM: artificial sequence
<220> FEATURE:
<223> OTHER INFORMATION: Dbait32Hc

<400> SEQUENCE: 4
gctgtgccca aacccagca aacaagccta ga                                    32

<210> SEQ ID NO 5
<211> LENGTH: 32
<212> TYPE: DNA
<213> ORGANISM: artificial sequence
<220> FEATURE:
<223> OTHER INFORMATION: Dbait32Hd

<400> SEQUENCE: 5
gctaggtctg tttggtggct ttgcagtggc ac                                   32

<210> SEQ ID NO 6
<211> LENGTH: 32
<212> TYPE: DNA
<213> ORGANISM: artificial sequence
<220> FEATURE:
<223> OTHER INFORMATION: nucleic acid molecule Ia
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 6
acgcacgggt gttgggtcgt tgttcggat ct                                    32

<210> SEQ ID NO 7
```

```
<211> LENGTH: 32
<212> TYPE: DNA
<213> ORGANISM: artificial sequence
<220> FEATURE:
<223> OTHER INFORMATION: nucleic acid molecule Ib
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 7
cgtaggtctg tttggtggct ttgcagtggc ac                                    32

<210> SEQ ID NO 8
<211> LENGTH: 32
<212> TYPE: DNA
<213> ORGANISM: artificial sequence
<220> FEATURE:
<223> OTHER INFORMATION: nucleic acid molecule Ic
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 8
gctaggcttg tttgctgggt tgtaggcaca gc                                    32

<210> SEQ ID NO 9
<211> LENGTH: 32
<212> TYPE: DNA
<213> ORGANISM: artificial sequence
<220> FEATURE:
<223> OTHER INFORMATION: nucleic acid molecule Id
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
```

```
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 9
gctgtgccca aacccagca aacaagccta ga                                     32

<210> SEQ ID NO 10
<211> LENGTH: 32
<212> TYPE: DNA
<213> ORGANISM: artificial sequence
<220> FEATURE:
<223> OTHER INFORMATION: nucleic acid molecule Ie
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: stem_loop
<222> LOCATION: (1)..(32)
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane + Lm = carboxamido oligoethylene glycol + C =
      single or double chain fatty acids, cholesterol, sugars, peptides
      or proteins

<400> SEQUENCE: 10
gctaggtctg tttggtggct ttgcagtggc ac                                    32

<210> SEQ ID NO 11
<211> LENGTH: 32
<212> TYPE: DNA
<213> ORGANISM: artificial sequence
<220> FEATURE:
<223> OTHER INFORMATION: nucleic acid molecule IIa
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: misc_feature
```

-continued

```
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 11
acgcacgggt gttgggtcgt ttgttcggat ct                                       32

<210> SEQ ID NO 12
<211> LENGTH: 32
<212> TYPE: DNA
<213> ORGANISM: artificial sequence
<220> FEATURE:
<223> OTHER INFORMATION: nucleic acid molecule IIb
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 12
cgtaggtctg tttggtggct ttgcagtggc ac                                       32

<210> SEQ ID NO 13
<211> LENGTH: 32
<212> TYPE: DNA
<213> ORGANISM: artificial sequence
<220> FEATURE:
<223> OTHER INFORMATION: nucleic acid molecule IIc
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane
```

-continued

```
<400> SEQUENCE: 13
gctaggcttg tttgctgggt tgtaggcaca gc                                32

<210> SEQ ID NO 14
<211> LENGTH: 32
<212> TYPE: DNA
<213> ORGANISM: artificial sequence
<220> FEATURE:
<223> OTHER INFORMATION: nucleic acid molecule IId
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 14
gctgtgccca acccagca aacaagccta ga                                 32

<210> SEQ ID NO 15
<211> LENGTH: 32
<212> TYPE: DNA
<213> ORGANISM: artificial sequence
<220> FEATURE:
<223> OTHER INFORMATION: nucleic acid molecule IIe
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<222> LOCATION: (1)..(1)
<223> OTHER INFORMATION: at the 5' end, Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 15
gctaggtctg tttggtggct ttgcagtggc ac                               32
```

-continued

```
<210> SEQ ID NO 16
<211> LENGTH: 32
<212> TYPE: DNA
<213> ORGANISM: artificial sequence
<220> FEATURE:
<223> OTHER INFORMATION: nucleic acid molecule IIIa
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3'end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 16
acgcacgggt gttgggtcgt tgttcggat ct                                      32

<210> SEQ ID NO 17
<211> LENGTH: 32
<212> TYPE: DNA
<213> ORGANISM: artificial sequence
<220> FEATURE:
<223> OTHER INFORMATION: nucleic acid molecule IIIb
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3'end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 17
cgtaggtctg tttggtggct ttgcagtggc ac                                     32

<210> SEQ ID NO 18
<211> LENGTH: 32
<212> TYPE: DNA
<213> ORGANISM: artificial sequence
<220> FEATURE:
```

```
<223> OTHER INFORMATION: nucleic acid molecule IIIc
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3'end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 18
gctaggcttg tttgctgggt tgtaggcaca gc                                   32

<210> SEQ ID NO 19
<211> LENGTH: 32
<212> TYPE: DNA
<213> ORGANISM: artificial sequence
<220> FEATURE:
<223> OTHER INFORMATION: nucleic acid molecule IIId
<220> FEATURE:
<221> NAME/KEY: misc_feature
<223> OTHER INFORMATION: note="at the 3' end of the complementary strand
      the three last nucleotides with phosphorothioate or
      methylphosphonate backbone"
<220> FEATURE:
<221> NAME/KEY: misc_feature
<223> OTHER INFORMATION: note= "the last nucleotide at the 3'end of the
      complementary strand is linked to Lm = carboxamido oligoethylene
      glycol + C = single or double chain fatty acids, cholesterol,
      sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
      backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
      tetradeoxythymidylate or 2,19-bis(phosphor)-8-hydraza-1-hydroxy-4-
      oxa-9-oxo-nonadecane

<400> SEQUENCE: 19
gctgtgccca aacccagca aacaagccta ga                                    32

<210> SEQ ID NO 20
<211> LENGTH: 32
<212> TYPE: DNA
<213> ORGANISM: artificial sequence
<220> FEATURE:
<223> OTHER INFORMATION: nucleic acid molecule IIIe
<220> FEATURE:
<221> NAME/KEY: misc_feature
<223> OTHER INFORMATION: note="at the 3' end of the complementary strand
      the three last nucleotides with phosphorothioate or
``` methylphosphonate backbone"
<220> FEATURE:
<221> NAME/KEY: misc_feature
<223> OTHER INFORMATION: note= "the last nucleotide at the 3'end of the
    complementary strand is linked to Lm = carboxamido oligoethylene
    glycol + C = single or double chain fatty acids, cholesterol,
    sugars, peptides or proteins
<220> FEATURE:
<221> NAME/KEY: modified_base
<222> LOCATION: (1)..(3)
<223> OTHER INFORMATION: mod_base= phosphorothioate or methylphosphonate
    backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =hexaethyleneglycol,
    tetradeoxythymidylate or 2,19-bis(phosphor)-8-hydraza-1-hydroxy-4-
    oxa-9-oxo-nonadecane

<400> SEQUENCE: 20
gctaggtctg tttggtggct ttgcagtggc ac                                    32

<210> SEQ ID NO 21
<211> LENGTH: 32
<212> TYPE: DNA
<213> ORGANISM: artificial sequence
<220> FEATURE:
<223> OTHER INFORMATION: nucleic acid molecule DT01
<220> FEATURE:
<221> NAME/KEY: misc_feature
<223> OTHER INFORMATION: note="at the 3' end of the complementary strand
    the three last nucleotides with phosphorothioate backbone"
<220> FEATURE:
<221> NAME/KEY: misc_feature
<222> LOCATION: (1)..(1)
<223> OTHER INFORMATION: at the 5' end,
    10-O-[1-propyl-3-N-carbamoylcholesteryl]-triethyleneglycol
    radical
<220> FEATURE:
<221> NAME/KEY: modified_base
<222> LOCATION: (1)..(3)
<223> OTHER INFORMATION: mod_base= phosphorothioate  backbone
<220> FEATURE:
<221> NAME/KEY: stem_loop
<222> LOCATION: (1)..(32)
<220> FEATURE:
<221> NAME/KEY: misc_feature
<222> LOCATION: (32)..(32)
<223> OTHER INFORMATION: loop L' =
    2,19-bis(phosphor)-8-hydraza-1-hydroxy-4-oxa-9-oxo-nonadecane

<400> SEQUENCE: 21
gctgtgccca caacccagca aacaagccta ga                                    32

<210> SEQ ID NO 22
<211> LENGTH: 32
<212> TYPE: DNA
<213> ORGANISM: artificial sequence
<220> FEATURE:
<223> OTHER INFORMATION: nucleic acid molecule IId
<220> FEATURE:
<221> NAME/KEY: misc_feature
<222> LOCATION: (1)..(1)
<223> OTHER INFORMATION: loop L' =
    1,19-bis(phospho)-8-hydraza-2-hydroxy-4-oxa-9-oxo-nonadecane
<220> FEATURE:
<221> NAME/KEY: stem_loop
<222> LOCATION: (1)..(32)
<220> FEATURE:
<221> NAME/KEY: misc_feature
<222> LOCATION: (30)..(32)
<223> OTHER INFORMATION: mod_base= phosphorothioate backbone -continued

<400> SEQUENCE: 22
tctaggcttg tttgctgggt tgtgggcaca gc        32

USE OF A COMBINATION OF DBAIT MOLECULE AND PARP INHIBITORS TO TREAT CANCER

CROSS-REFERENCE TO RELATED APPLICATIONS

This application is a continuation of U.S. Ser. No. 15/746,806, filed Jan. 23, 2018, now U.S. Pat. No. 10,563,197, which is the U.S. national stage application of International Patent Application No. PCT/EP2016/067479, filed Jul. 22, 2016.

The Sequence Listing for this application is labeled "Seq-List-replace.txt" which was created on Feb. 24, 2021 and is 16 KB. The entire content of the sequence listing is incorporated herein by reference in its entirety.

FIELD OF THE INVENTION

The present invention relates to the field of medicine, in particular of oncology.

BACKGROUND OF THE INVENTION

The Poly(ADP ribose)polymerase PARP1 (and PARP2) is an enzyme that binds DNA damage and promotes DNA repair by forming polymers of ADP-ribose which attract repair enzymes. PARP is the key enzyme of single-strand breaks by Base Excision Repair pathway. If left unrepaired, the single-strand breaks convert to double strand breaks during replication that are essentially repaired by Homologous recombination. Therefore, inhibiting PARP is lethal in cells deficient to Homologous Recombination. This observation led to the development of PARP inhibitors to treat cancers that already have mutations disabling their Homologous Recombination capacity.

Two main enzymes are targeted by the PARP inhibitors: PARP1 and PARP2. Under normal conditions, PARP1 and PARP2 are released from DNA once the repair process is underway. However, when they are bound to some PARP inhibitors, PARP1 and PARP2 become trapped on DNA. The trapped PARP-DNA complexes are more toxic to cells than the unrepaired single-strand DNA breaks. There are two classes of PARP inhibitors: (i) catalytic inhibitors that act mainly to inhibit PARP enzyme activity and do not trap PARP proteins on DNA, and (ii) bound inhibitors that block PARP enzyme activity and prevent its release from the Damage site. Though many PARP inhibitors have been developed, their classification in type (i) or (ii) is not clear. It has been proposed that Veliparib could be type (i) and Olaparib, Niraparib, BM673 could belong to type (ii). Moreover, as PARP is involved in many cellular processes, the mechanism of action of PARP inhibitors in tumor cells remains not completely elucidated.

Patients are currently considered for PARP inhibitor trials only if they have a particular tumor type (e.g., high-grade serous ovarian cancer or triple negative brain cancer) or their cancer could belong to a relevant molecular subtype (e.g., BRCA1/2-mutated breast, ovarian, pancreatic, or prostate cancer).

Though PARP inhibitor (PARPi) monotherapy showed promising efficacy and safety profiles in the clinic, their major limitations are the necessity of HR deficiency and the rapid emergence of resistance. Many tumors that initially responded to PARPi treatments finally relapsed through compensatory mutations restoring the HR activity or stimulating the activity of alternative repair pathways.

Accordingly, the use of PARP inhibitors is limited to particular tumor types and can't be used for treating any cancer.

SUMMARY OF THE INVENTION

The present invention provides a combined treatment allowing one to use PARP inhibitors for treating any kind of cancers, in particular without being limited to those associated with Homologous Recombination deficiency. In addition, the present invention provides a combination of PARP inhibitor with nucleic acid molecules as defined herein, leading to a synergistic effect against tumors. Accordingly, the present invention relates to a pharmaceutical composition comprising a PARP inhibitor and a nucleic acid molecule as defined herein, in particular for use for treating cancer.

The present invention also relates to a PARP inhibitor for use for treating cancer in combination with a nucleic acid molecule as defined herein or to a nucleic acid molecule as defined herein for use for treating cancer in combination with a PARP inhibitor.

It further relates to a kit comprising a PARP inhibitor and a nucleic acid molecule as defined herein as a combined preparation for simultaneous, separate or sequential use, in particular in the treatment of cancer.

Preferably, the nucleic acid molecule has at least one free end and a DNA double stranded portion of 6-200 bp with less than 60% sequence identity to any gene in a human genome.

More preferably, the nucleic acid molecule has one of the following formulae:

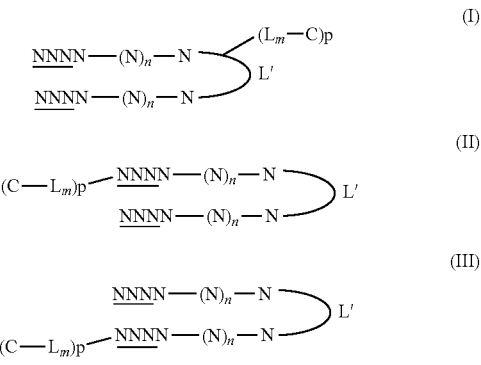

wherein N is a deoxynucleotide, n is an integer from 1 to 195, the underlined N refers to a nucleotide having or not a modified phosphodiester backbone, L' is a linker, C is a molecule facilitating endocytosis preferably selected from a lipophilic molecule and a ligand which targets cell receptor enabling receptor mediated endocytosis, L is a linker, m and p, independently, are an integer being 0 or 1.

More specifically, the nucleic acid molecule has one of the following formulae:

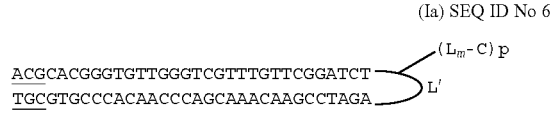

(IIa) SEQ ID No 11
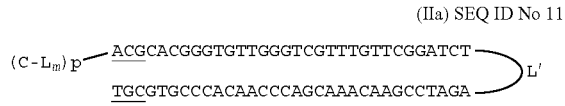

(IIIa) SEQ ID No 16
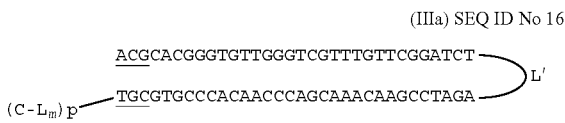

(Ib) SEQ ID No 7
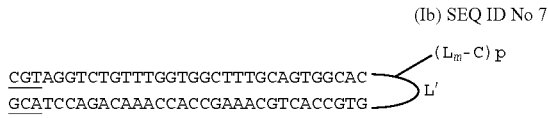

(IIb) SEQ ID No 12
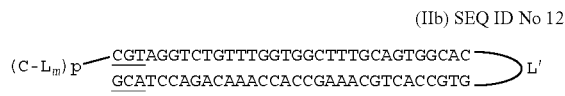

(IIIb) SEQ ID No 17
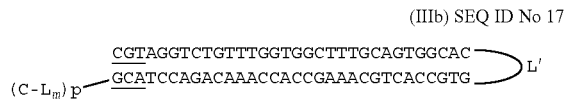

(Ic) SEQ ID No 8
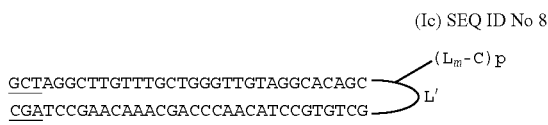

(IIc) SEQ ID No 13
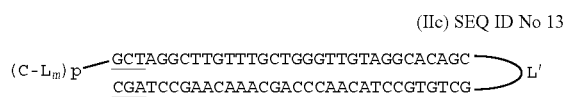

(IIIc) SEQ ID No 18
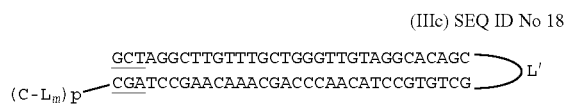

(Id) SEQ ID No 9
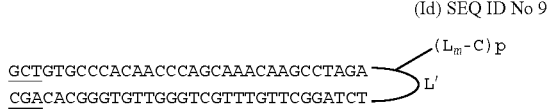

SEQ ID No 14
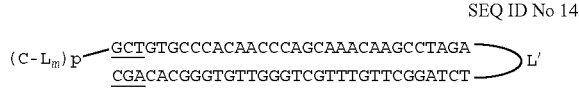

(IId) SEQ ID No 22

(IIId) SEQ ID No 19
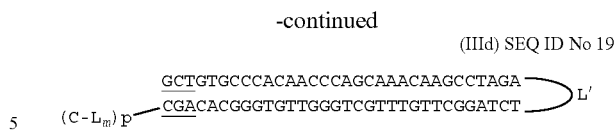

(Ie) SEQ ID No 10
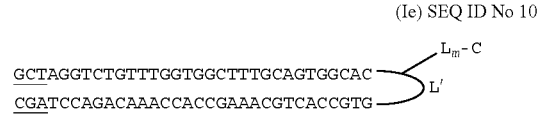

(IIe) SEQ ID No 15
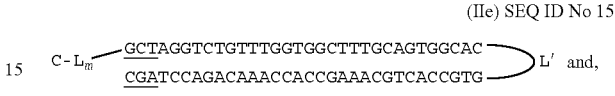

(IIIe) SEQ ID No 20
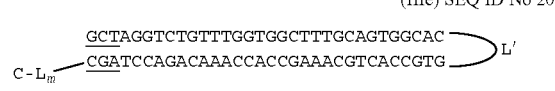

wherein the underlined nucleotide refers to a nucleotide having a phosphorothioate or methylphosphonate backbone, the linked L' is selected from the group consisting of hexaethyleneglycol, tetradeoxythymidylate (T4), 1,19-bis (phospho)-8-hydraza-2-hydroxy-4-oxa-9-oxo-nonadecane and 2,19-bis(phosphor)-8-hydraza-1-hydroxy-4-oxa-9-oxo-nonadecane; m is 1 and L is a carboxamido oligoethylene glycol, C is selected from the group consisting of single or double chain fatty acids such as octadecyl and dioleoyl, cholesterol, tocopherol, folic acid, sugar such as galactose and mannose and their oligosaccharide, peptide such as RGD and bombesin and protein such as integrin, preferably cholesterol or tocopherol.

In a preferred embodiment, the nucleic acid molecule is selected from the group consisting of (Id) SEQ ID No 9
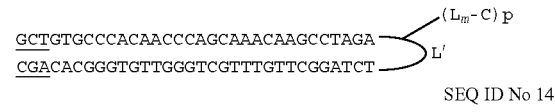

SEQ ID No 14
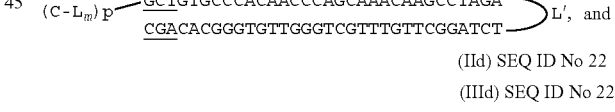

(IId) SEQ ID No 22

(IIId) SEQ ID No 22
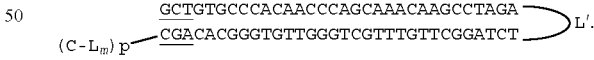

More preferably, the molecule facilitating endocytosis is cholesterol or tocopherol.

In a very specific embodiment, the nucleic acid molecule has the following formula SEQ ID No 21

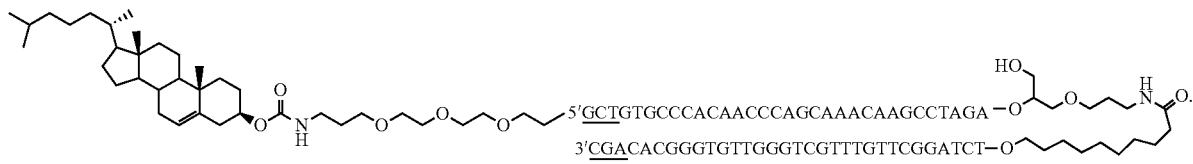

In another very specific embodiment, the nucleic acid molecule has the following formula

SEQ ID No 14

(IId) SEQ ID No 22 wherein C is a cholesteryl, Lm is a tetraethylene glycol, p is 1 and L' is 1,19-bis(phospho)-8-hydraza-2-hydroxy-4-oxa-9-oxo-nonadecane.

Preferably, the PARP inhibitor is selected from the group consisting of rucaparib (AGO 14699, PF-01367338), olaparib (AZD2281), veliparib (ABT888), iniparib (BSI 201), niraparib (MK 4827), talazoparib (BMN673), AZD 2461, CEP 9722, E7016, INO-1001, LT-673, MP-124, NMS-P118, XAV939, analogs, derivatives or a mixture thereof. More preferably, the PARP inhibitor is selected from the group consisting of AZD2281 (Olaparib), ABT888 (Veliparib), BMN673, BSI-21 (Iniparib), AZD 2461, MK-4827 (Niraparib), and AG 014699 (Rucaparib).

In a particular aspect, the PARP inhibitor is used with a sub-therapeutic amount.

All cancer type can be treated. More preferably, the cancer is selected from leukemia, lymphoma, sarcoma, melanoma, and cancers of the head and neck, kidney, ovary, pancreas, prostate, thyroid, lung, in particular small-cell lung cancer, and non-small-cell lung cancer, esophagus, breast, bladder, colorectum, liver, cervix, and endometrial and peritoneal cancers. In particular, the cancer is a solid cancer. In a particular aspect, the cancer is a metastatic cancer or high-grade or advanced cancer. In a particular embodiment, the cancer is selected from leukemia, lymphoma, melanoma, sarcoma, cancer of the head and neck, breast cancer, brain cancer, colorectum cancer, and cancer of cervix.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

(FIG. 11A) Cytotoxicity of AsiDNA toward various isogenic DT40 cell lines. (FIG. 11B) Comparison of cell survival to AsiDNA in DT40 cells wild-type (WT; black) or PARP KO (red) alone (continuous line) or in combination with veliparib 1 µM (blue discontinuous line). Survivals were monitored by ATPlite 1-step kit (72 hours after treatment) in various mutant DT40 cells as described in (36). Survival is expressed as % of non-treated cells. Results are represented as mean survival±SEM for three independent experiments.

DETAILED DESCRIPTION OF THE INVENTION

Figure 1:
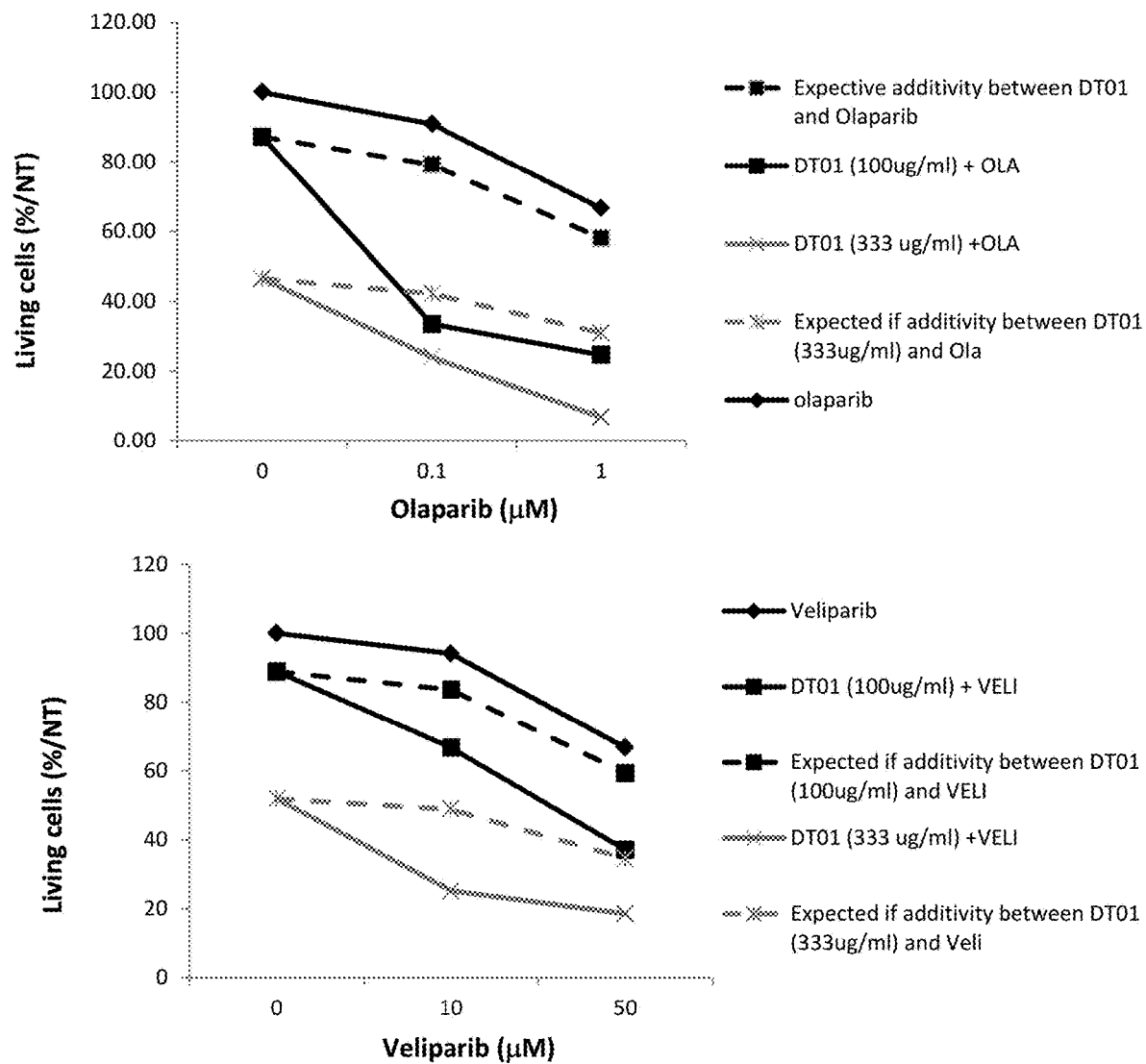
FIG. 1: Examples of supra-additivity of the combination of Olaparib and Veliparib with DT01 measured by the percentage of living cells at several doses of olaparib (OLA), veliparib (VELI) and DT01.

Accordingly, the present invention relates to:
- a pharmaceutical composition comprising a PARP inhibitor and a nucleic acid molecule as defined herein, and optionally a pharmaceutically acceptable carrier, in particular for use in the treatment of cancer;
- a product or kit containing a PARP inhibitor and a nucleic acid molecule as defined herein as a combined preparation for simultaneous, separate or sequential use, in particular in the treatment of cancer;
- a combined preparation which comprises a PARP inhibitor and a nucleic acid molecule as defined herein for simultaneous, separate or sequential use, in particular in the treatment of cancer;
- a pharmaceutical composition comprising a PARP inhibitor for the use in the treatment of cancer in combination with a treatment with a nucleic acid molecule as defined herein;
- a pharmaceutical composition comprising a nucleic acid molecule as defined herein for the use in the treatment of cancer in combination with a treatment with a PARP inhibitor;
- the use of a pharmaceutical composition comprising a PARP inhibitor for the manufacture of a medicament for the treatment of cancer in combination with a treatment with a nucleic acid molecule as defined herein;
- the use of a pharmaceutical composition comprising a nucleic acid molecule as defined herein for the manufacture of a medicament for the treatment of cancer in combination with a treatment with a PARP inhibitor;
- the use of a pharmaceutical composition comprising a PARP inhibitor and a nucleic acid molecule as defined herein, and optionally a pharmaceutically acceptable carrier for the manufacture of a medicament for the treatment of cancer;
- a method for treating a cancer in a subject in need thereof, comprising administering an effective amount of a pharmaceutical composition comprising a) nucleic acid molecule as defined herein, b) a PARP inhibitor, and a pharmaceutically acceptable carrier;
- a method for treating a cancer in a subject in need thereof, comprising administering an effective amount of a pharmaceutical composition comprising a PARP inhibitor, and an effective amount of a pharmaceutical composition comprising a nucleic acid molecule as defined herein;
- a method for treating a cancer in a subject in need thereof, comprising administering an effective amount of a pharmaceutical composition comprising a PARP inhibitor and a nucleic acid molecule as defined herein.

The terms "kit", "product" or "combined preparation", as used herein, defines especially a "kit of parts" in the sense that the combination partners as defined above can be dosed independently or by use of different fixed combinations with distinguished amounts of the combination partners, i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partners to be administered in the combined preparation can be varied. The combination partners can be administered by the same route or by different routes.

Within the context of the invention, the term treatment denotes curative, symptomatic, and preventive treatment. Pharmaceutical compositions, kits, products and combined preparations of the invention can be used in humans with existing cancer or tumor, including at early or late stages of progression of the cancer. The pharmaceutical compositions, kits, products and combined preparations of the invention will not necessarily cure the patient who has the cancer but will delay or slow the progression or prevent further progression of the disease, ameliorating thereby the patients' condition. In particular, the pharmaceutical compositions, kits, products and combined preparations of the invention reduce the development of tumors, reduce tumor burden, produce tumor regression in a mammalian host and/or prevent metastasis occurrence and cancer relapse. In treating the cancer, the pharmaceutical composition of the invention is administered in a therapeutically effective amount.

By "therapeutically effective amount" it is meant the quantity of the pharmaceutical composition of the invention which prevents, removes or reduces the deleterious effects of cancer in mammals, including humans, alone or in combination with the other active ingredients of the pharmaceutical composition, kit, product or combined preparation. It is understood that the administered dose may be lower for each compound in the composition to the "therapeutic effective amount" define for each compounds used alone or in combination with other treatments than the combination described here. The "therapeutic effective amount" of the composition will be adapted by those skilled in the art according to the patient, the pathology, the mode of administration, etc.

Whenever within this whole specification "treatment of a cancer" or the like is mentioned with reference to the pharmaceutical composition of the invention, there is meant:

a) a method for treating a cancer, said method comprising administering a pharmaceutical composition of the invention to a subject in need of such treatment; b) the use of a pharmaceutical composition of the invention for the treatment of a cancer; c) the use of a pharmaceutical composition of the invention for the manufacture of a medicament for the treatment of a cancer; and/or d) a pharmaceutical composition of the invention for use in the treatment a cancer.

The pharmaceutical compositions contemplated herein may include a pharmaceutically acceptable carrier in addition to the active ingredient(s). The term "pharmaceutically acceptable carrier" is meant to encompass any carrier (e.g., support, substance, solvent, etc.) which does not interfere with effectiveness of the biological activity of the active ingredient(s) and that is not toxic to the host to which it is administered. For example, for parental administration, the active compounds(s) may be formulated in a unit dosage form for injection in vehicles such as saline, dextrose solution, serum albumin and Ringer's solution.

The pharmaceutical composition can be formulated as solutions in pharmaceutically compatible solvents or as emulsions, suspensions or dispersions in suitable pharmaceutical solvents or vehicle, or as pills, tablets or capsules that contain solid vehicles in a way known in the art. Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations suitable for parental administration conveniently comprise a sterile oily or aqueous preparation of the active ingredient which is preferably isotonic with the blood of the recipient. Every such formulation can also contain other pharmaceutically compatible and nontoxic auxiliary agents, such as, e.g. stabilizers, antioxidants, binders, dyes, emulsifiers or flavouring substances. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. Methods for the safe and effective administration of most of these chemotherapeutic agents are known to those skilled in the art. In addition, their administration is described in the standard literature.

PARP Inhibitor

The term "PARP" as used herein refers to Poly (ADP-ribose) polymerase. PARP catalyzes the conversion of β-nicotinamide adenine dinucleotide ($NAD^+$) into nicotinamide and poly-ADP-ribose (PAR). PARP is a key molecule in the repair of DNA single-strand breaks (SSBs). As used herein, the term "PARP" (EC 2.4.2.30) is equivalent to "PARS" (for poly(ADP-ribose) synthetase), "ADPRT" (for NADrprotein (ADP-ribosyl) transferase (polymerising)), or "pADPRT" (for poly(ADP-ribose) transferase).

As used herein, the term "PARP inhibitor" refers to any compound which has the ability to decrease the activity of a poly (ADP-ribose) polymerase (PARP). PARP inhibition relies mainly on two different mechanisms: (i) catalytic inhibition that act mainly by inhibiting PARP enzyme activity and (ii) bound inhibition that block PARP enzyme activity and prevent its release from the damage site. Bound inhibitors are more toxic to cells than catalytic inhibitors. PARP inhibitors according to the inventions are preferably catalytic and/or bound inhibitors.

In a preferred embodiment, the PARP inhibitor is an inhibitor of any enzyme of the PARP family, preferentially PARP1 and/or PARP2.

The PARP activity can be determined by a variety of techniques well known by the skilled person. Usually, these techniques comprise measuring the incorporation of a labeled poly(ADP-ribose) onto histone proteins. Commercial kits for such techniques are available (see for example, Tervigen's kits with biotinylated poly(ADP-ribose)). Other methods may also be used such as the one developed by Putt K S et al (Anal Biochem, 326(1):78-86, 2004), the disclosure of which is hereby incorporated by reference in its entirety. These methods are ideal for the determination of IC50 values of known or suspected PARP inhibitors.

Many PARP inhibitors are known and, thus, can be synthesized by known methods from starting materials that are known, may be available commercially, or may be prepared by methods used to prepare corresponding compounds in the literature.

Examples of suitable PARP inhibitors according to the invention include, but are not limited to, olaparib (AZD-2281, 4-[(3-[(4-cyclopropylcarbonyl)piperazin-4-yl]carbonyl)-4-fluorophenyl]methyl(2H)-phthalazin-1-one), veliparib (ABT-888, CAS 912444-00-9, 2-((fi)-2-methylpyrrolidin-2-yl)-lW-benzimidazole-4-carboxamide), CEP-8983 (ll-methoxy-4,5,6,7-tetrahydro-1H-cyclopenta[a]pyrrolo[3,4-c]carbazole-1,3(2H)-dione) or a prodrug thereof (e.g. CEP-9722), rucaparib (AG014699, PF-01367338, 8-Fluoro-2-{4-[(methylamino)methyl]phenyl}-1,3,4,5-tetrahydro-6H-azepino[5,4,3-cd]indol-6-one), E7016 (GPI-21016, 10-((4-Hydroxypiperidin-1-yl)methyl)chromeno-[4,3,2-de]phthalazin-3(2H)-one), talazoparib (BMN-673, (8S,9R)-5-fluoro-8-(4-fluorophenyl)-9-(1-methyl-1H-1,2,4-triazol-5-yl)-8,9-dihydro-2H-pyrido[4,3,2de]phthalazin-3 (7-H)-one), INO-1001 (4-phenoxy-3-pyrrolidin-1-yl-5-sulfamoyl-benzoic acid), KU0058684 (CAS 623578-11-0), niraparib (MK 4827, Merck & Co Inc), iniparib (BSI 201), iniparib-met (C-nitroso metabolite of Iniparib), CEP 9722 (Cephalon Inc), LT-673, MP-124, NMS-P118, XAV939, AZD 2461, nicotinamides, 5-methyl nicotinamide, 4-Amino-1,8-naphthalimide, picolinamide, benzamides, 3-substituted benzamides, 3-methoxybenzamide, 3-hydroxybenzamide, 3-aminobenzamide, 3-chloroprocainamide, 3-nitrosobenzamide, 4-aminobenzamide, 2-aminobenzamide, methyl 3,5-diiodo-4-(4'-methoxyphenoxy) benzoate, methyl-3,5-diiodo-4-(4'-methoxy-3',5'-diiodophenoxy) benzoate, cyclic benzamides, 1,5-di[(3-carbamoylphenyl)aminocarbonyloxy] pentane, indoles, benzimidazoles, benzoxazole-4-carboxamides, benzimidazole-4-carboxamides, 2-substituted benzoxazole 4-carboxamides, 2-substituted benzimidazole 4-carboxamides, 2-aryl benzimidazole 4-carboxamides, 2-cycloalkylbenzimidazole-4-carboxamides, 2-(4-hydroxphenyl) benzimidazole A-carboxamide, quinoxalinecarboxamides, imidazopyridinecarboxamides, 2-phenylindoles, 2-substituted benzoxazoles, 2-phenyl benzoxazole, 2-(3-methoxyphenyl) benzoxazole, 2-substituted benzimidazoles, 2-phenyl benzimidazole, 2-(3-methoxyphenyl) benzimidazole, 1,3,4,5-tetrahydro-azepino[5,4,3-cd]indol-6-one, azepinoindoles, azepinoindolones, 1,5-dihydro-azepino[4,5,6-cd]indolin-6-one, dihydrodiazapinoindolinones, 3-substituted dihydrodiazapinoindolinones, 3-(4-trifluoromethylphenyl)-dihydrodiazapinoindolinone, tetrahydrodiazapinoindolinone, 5,6-dihydroimidazo[4,5, 1-j, k][1,4]benzodiazopin-7(4H)-one, 2-phenyl-5,6-dihydro-imidazo[4,5,1-jk][1,4]benzodiazepin-7(4H)-one, 2,3-dihydro-isoindol-1-one, benzimidazole-2-piperazine, benzimidazole-2-piperazine heterocyclic derivatives, 4-iodo-3-nitrobenzamide, benzopyrones, 1,2-benzopyrone 6-nitrosobenzopyrone, 6-nitroso 1,2-benzopyrone, 5-iodo-6-aminobenzopyrone, benzoylurea, quinolone, isoquinolone, isoquinolinones, dihydroisoquinolinones, 2H-isoquinolin-1-ones, 3H-quinazolin-4-ones, 5-substituted dihydroisoquinolinones, 5-hydroxy dihydroisoquinolinone, 5-methyl dihydroisoquinolinone, 5-hydroxy isoquinolinone, 5-amino isoquinolin-1-one, 5-dihydroxyisoquinolinone, 1,5-dihydroxyisoquinoline, 1,5-isoquinolinediol, 4-hydroxyquinazoline, substituted thiazolyl-isoquinolinones, substituted oxazoyl-isoquinolinones, tetrahydro-2H-isoquinolin-1-one, 3,4-dihydroisoquinolin-1(2H)-ones, 3,4-dihydro-5-methoxy-isoquinolin-1(2H)-one, 3,4-dihydro-5-methyl-1(2H)isoquinolinone, 3H-quinazolin-4-one, isoquinolin-1(2H)-ones, 3,4 dihydroisoquinolin-1(2H)-one, 4-carboxamido-benzimidazole, substituted 6-cyclohexylalkyl substituted 2-quinolinones, substituted 6-cyclohexylalkyl substituted 2-quinoxalinones, 7-phenylalkyl substituted 2-quinolinones, 7-phenylalkyl substituted 2-quinoxalinones, 6-substituted 2-quinolinones, 6-substituted 2-quinoxalinones, 1-(arylmethyl)quinazoline-2,4(1H,3H)-dione, 4,5-dihydro-imidazo[4,5,1-ij]quinolin-6-ones, 1,6-naphthyridine-5(6H)-ones, 1,8-naphthalimides, 4-amino-1,8-naphthalimides, 3,4-dihydro-5-[4-1(1-piperidinyl)butoxy]-1(2H)-isoquinolinone, 2,3-dihydrobenzo[de]isoquinolin-1-one, 1-1 1b-dihydro-[2H]benzopyrano[4,3,2-de]isoquinolin-3-one, tetracyclic lactams, benzpyranoisoquinolinones, benzopyrano[4,3,2-de]isoquinolinone, quinazolines, quinazolinones, quinazolinediones, A-hydroxyquinazoline, 2-substituted quinazolines, 8-hydroxy-2-methylquinazolin-4-(3H)one, phthalazines, phthalazinones, phthalazin-1(2H)-ones, 5-methoxy-4-methyl-1(2) phthalazinones, 4-substituted phthalazinones, 4-(1-piperazinyl)-1 (2H)-phthalazinone, tetracyclic benzopyrano[4,3,2-de]phthalazinones and tetracyclic indeno[1,2,3-de]phthalazinones, tricyclic phthalazinones, 2-aminophthalhydrazide, phthalazinone ketone, dihydropyridophthalazinone, 6-substituted 5-arylamino-1 h-pyridine-2-ones, pyridazinones, tetrahydropyridopyridazinone, tetraaza phenalen-3-one, thieno[2,3-c]isoquinolin-5-one (TIQ-A), 2,5-diazabicyclo[2.2.1]heptane, pyrimidoimidazole, isoindolinones, phenanthridines, phenanthridinones, 5 [H]phenanthridin-6-one, substituted 5[H] phenanthridin-6-ones, 2,3-substituted 5 [H]phenanthridin-6-ones, sulfonamide/carbamide derivatives of 6(5H)phenanthridinones, thieno[2, 3-c]isoquinolones, 9-amino thieno[2,3-c]isoquinolone, 9-hydroxythieno[2, 3-c]isoquinolone, 9-methoxythieno[2,3-c]isoquinolone, N-(6-oxo-5,6-dihydrophenanthridin-2-yl]-2-(N,N-dimethylamino}acetamide, substituted 4,9-dihydrocyclopenta[imn]phenanthridine-5-ones, unsaturated hydroximic acid derivatives, O-(3-piperidino-2-hydroxy-1-propyl)nicotinic amidoxime, O-(2-hydroxy-3-piperidino-propyl)-3-carboxylic acid amidoxime, pyridazines, pyrazinamide, BGB-290, PF-1367338 (Pfizer Inc), AG014699 (Pfizer, Inc.), KU-59436 (KuDOS/AstraZeneca PJ34, 4-amino-1,8-naphthalimide (Trevigen), 6(5H)-phenanthridinone (Trevigen), NU1025, 4-HQN, BGP-15, A-966492, GPI21016, 6(5H)-phenanthridinone (Phen), theobromine, theophylline, caffeine, methylxanthines, thymidine, 3-aminophtalhydrazide, analogs, derivatives or a mixture thereof.

Additional PARP inhibitors are described for example in WO14201972, WO14201972, WO12141990, WO10091140, WO9524379, WO09155402, WO009046205, WO08146035, WO08015429, WO0191796, WO0042040, US2006004028, EP2604610, EP1802578, CN104140426, CN104003979, US060229351, U.S. Pat. No. 7,041,675, WO07041357, WO2003057699, U.S. Ser. No. 06/444,676, US20060229289, US20060063926, WO2006033006, WO2006033007, WO03051879, WO2004108723, WO2006066172, WO2006078503, US20070032489, WO2005023246, WO2005097750, WO2005123687, WO2005097750, U.S. Pat. Nos. 7,087,637, 6,903,101, WO20070011962, US20070015814, WO2006135873, UA20070072912, WO2006065392, WO2005012305, WO2005012305, EP412848, EP453210, EP454831, EP879820, EP879820, WO030805, WO03007959, U.S. Pat. No. 6,989,388, US20060094746, EP1212328, WO2006078711, U.S. Ser. No. 06/426,415, U.S. Ser. No. 06/514,983, EP1212328, US20040254372, US20050148575, US20060003987, U.S. Ser. No. 06/635,642, WO200116137, WO2004105700, WO03057145A2, WO2006078711, WO2002044157, US20056924284, WO2005112935, US20046828319, WO2005054201, WO2005054209, WO2005054210, WO2005058843, WO2006003146, WO2006003147, WO2006003148, WO2006003150, WO2006003146, WO2006003147, UA20070072842, U.S. Ser. No. 05/587, 384, US20060094743, WO2002094790, WO2004048339, EP1582520, US20060004028, WO2005108400, U.S. Pat. No. 6,964,960, WO20050080096, WO2006137510, UA20070072841, WO2004087713, WO2006046035, WO2006008119, WO06008118, WO2006042638, US20060229289, US20060229351, WO2005023800, WO1991007404, WO2000042025, WO2004096779, U.S. Pat. No. 6,426,415, WO2068407, U.S. Pat. No. 6,476,048, WO2001090077, WO2001085687, WO2001085686, WO2001079184, WO2001057038, WO2001023390, WO01021615A1, WO2001016136, WO2001012199, WO95024379, WO200236576, WO2004080976, WO2007149451, WO2006110816, WO2007113596, WO2007138351, WO2007144652, WO2007144639, WO2007138351, WO2007144637, Banasik et al. (J. Biol. Chem., 267:3, 1569-75, 1992), Banasik et al. (Molec. Cell. Biochem, 138:185-97, 1994), Cosi et al. (Expert Opin. Ther. Patents 12 (7), 2002), Southan and Szabo (Curr Med Chem, 10 321-340, 2003), Underhill C. et al. (Annals of Oncology, doi:10.1093/annonc/mdq322, pp 1-12, 2010), Murai J. et al. (J. Pharmacol. Exp. Ther., 349:408-416, 2014), all these patents and publications being hereby incorporated by reference in their entirety.

In a preferred embodiment, the PARP inhibitor compound is selected from the group consisting of rucaparib (AG014699, PF-01367338), olaparib (AZD2281), veliparib (ABT888), iniparib (BSI 201), niraparib (MK 4827), talazoparib (BMN673), AZD 2461, CEP 9722, E7016, INO-1001, LT-673, MP-124, NMS-P118, XAV939, analogs, derivatives or a mixture thereof.

In an even more preferred embodiment, the PARP inhibitor is selected from the group consisting of rucaparib (AG014699, PF-01367338), olaparib (AZD2281), veliparib (ABT888), iniparib (BSI 201), niraparib (MK 4827), talazoparib (BMN673), AZD 2461, analogs, derivatives or a mixture thereof.

Nucleic Acid Molecules

The nucleic acid molecules for use in the present invention, conjugated or not, can be described by the following formulae:

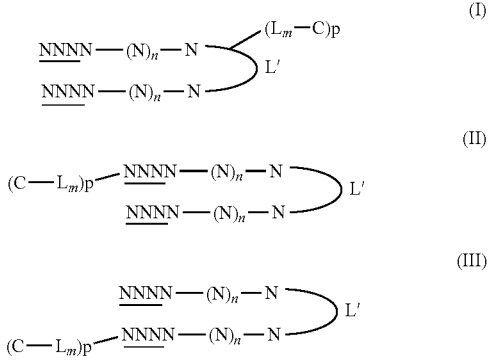

(I)

(II)

(III)

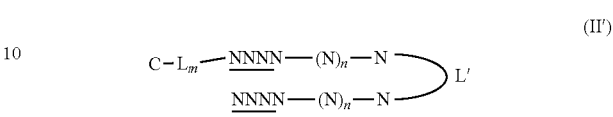

wherein N is a nucleotide, n is an integer of at least 1, the underlined $\underline{N}$ refers to a nucleotide having or not a modified phosphodiester backbone, L' is a linker, C is a molecule facilitating endocytosis, L is a linker, m and p, independently, are an integer being 0 or 1. In Formulae (II) and (III), C-$L_m$ is respectively linked to the 5' end or the 3' end of the nucleotide. In formula (I-III), C-$L_m$ is preferably linked to L' through a disulfide bond (S—S). When the molecule is conjugated, p is 1. Preferably, the underlined $\underline{N}$ refers to a nucleotide having a modified phosphodiester backbone.

In preferred embodiments, the molecule of formula (I), (II) or (III) has one or several of the following features:
- N is a deoxynucleotide, preferably selected from the group consisting of A (adenine), C (cytosine), T (thymine) and G (guanine) and selected so as to avoid occurrence of a CpG dinucleotide and to have less than 80% or 70%, even less than 60% or 50% sequence identity to any gene in a human genome; and/or,
- n is an integer from 1 to 195, preferably from 3 to 195, from 23 to 195, or from 25 to 195, optionally from 1 to 95, from 2 to 95, from 3 to 95, from 5 to 95, from 15 to 195, from 19-95, from 21 to 95, from 23 to 95, from 25 to 95, from 27 to 95, from 1 to 45, from 2 to 35, from 3 to 35, from 5 to 35, from 15 to 45, from 19 to 45, from 21 to 45, or from 27 to 45. In a particularly preferred embodiment, n is 27; and/or,
- the underlined $\underline{N}$ refers to a nucleotide having or not a phosphorothioate or methylphosphonate backbone, more preferably a phosphorothioate backbone; preferably, the underlined $\underline{N}$ refers to a nucleotide having a modified phosphodiester backbone; and/or,
- the linked L' is selected from the group consisting of hexaethyleneglycol, tetradeoxythymidylate (T4), 1,19-bis(phospho)-8-hydraza-2-hydroxy-4-oxa-9-oxo-nonadecane and 2,19-bis(phosphor)-8-hydraza-1-hydroxy-4-oxa-9-oxo-nonadecane; and/or,
- m is 1 and L is a carboxamido polyethylene glycol, more preferably carboxamido triethylene glycol or carboxamido tetraethylene glycol; and/or,
- C is selected from the group consisting of a cholesterol, single or double chain fatty acids such as octadecyl, oleic acid, dioleoyl or stearic acid, or ligand (including peptide, protein, aptamer) which targets cell receptor such as folic acid, tocopherol, sugar such as galactose and mannose and their oligosaccharide, peptide such as RGD and bombesin, and protein such transferring and integrin, preferably is a cholesterol or a tocopherol, still more preferably a cholesterol.

Preferably, C-Lm is a triethyleneglycol linker (10-O-[1-propyl-3-N-carbamoylcholesteryl]-triethyleneglycol radical. Alternatively, C-Lm is a tetraethyleneglycol linker (10-O-[1-propyl-3-N-carbamoylcholesteryl]-tetraethyleneglycol radical.

In a preferred embodiment, the conjugated Dbait molecule or hairpin nucleic acid molecule has the following formula:

(II')

with the same definition than formulae (I), (II), (II') and (III) for N, $\underline{N}$, n, L, L', C and m.

In a particular embodiment, the nucleic acid molecules can be Dbait molecules such as those extensively described in PCT patent applications WO2005/040378, WO2008/034866 and WO2008/084087, the disclosure of which is incorporated herein by reference.

Dbait molecules may be defined by a number of characteristics necessary for their therapeutic activity, such as their minimal length, the presence of at least one free end, and the presence of a double stranded portion, preferably a DNA double stranded portion. As will be discussed below, it is important to note that the precise nucleotide sequence of Dbait molecules does not impact on their activity. Furthermore, Dbait molecules may contain a modified and/or non-natural backbone.

Preferably, Dbait molecules are of non-human origin (i.e., their nucleotide sequence and/or conformation (e.g., hairpin) does not exist as such in a human cell), most preferably of synthetic origin. As the sequence of the Dbait molecules plays little, if any, role, Dbait molecules have preferably no significant degree of sequence homology or identity to known genes, promoters, enhancers, 5'- or 3'-upstream sequences, exons, introns, and the like. In other words, Dbait molecules have less than 80% or 70%, even less than 60% or 50% sequence identity to any gene in a human genome. Methods of determining sequence identity are well known in the art and include, e.g., Blast. Dbait molecules do not hybridize, under stringent conditions, with human genomic DNA. Typical stringent conditions are such that they allow the discrimination of fully complementary nucleic acids from partially complementary nucleic acids.

In addition, the sequence of the Dbait molecules is preferably devoid of CpG in order to avoid the well known toll-like receptor-mediated immunological reactions.

The length of Dbait molecules may be variable, as long as it is sufficient to allow appropriate binding of Ku protein complex comprising Ku and DNA-PKcs proteins. It has been showed that the length of Dbait molecules must be greater than 20 bp, preferably about 32 bp, to ensure binding to such a Ku complex and allowing DNA-PKcs activation. Preferably, Dbait molecules comprise between 20-200 bp, more preferably 24-100 bp, still more preferably 26-100, and most preferably between 24-200, 25-200, 26-200, 27-200, 28-200, 30-200, 32-200, 24-100, 25-100, 26-100, 27-100, 28-100, 30-100, 32-200 or 32-100 bp. For instance, Dbait molecules comprise between 24-160, 26-150, 28-140, 28-200, 30-120, 32-200 or 32-100 bp. By "bp" is intended that the molecule comprise a double stranded portion of the indicated length.

In a particular embodiment, the Dbait molecules having a double stranded portion of at least 32 pb, or of about 32 bp, comprise the same nucleotide sequence than Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5). Optionally, the Dbait molecules have the same nucleotide composition than Dbait32, Dbait32Ha, Dbait32Hb, Dbait32Hc or Dbait32Hd but their nucleotide sequence is different. Then, the Dbait molecules comprise one strand of the double stranded portion with 3 A, 6 C, 12 G and 11 T. Preferably, the sequence of the Dbait molecules does not contain any CpG dinucleotide.

Alternatively, the double stranded portion comprises at least 16, 18, 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5). In a more particular embodiment, the double stranded portion consists in 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5).

The nucleic acid as disclosed herein must have at least one free end, as a mimic of DSB. Said free end may be either a free blunt end or a 5'-/3'-protruding end. The "free end" refers herein to a nucleic acid molecule, in particular a double-stranded nucleic acid portion, having both a 5' end and a 3' end or having either a 3'end or a 5' end. Optionally, one of the 5' and 3' end can be used to conjugate the nucleic acid molecule or can be linked to a blocking group, for instance a or 3'-3'nucleotide linkage.

In an alternative embodiment, the nucleic acid molecules contain two free ends and can be linear. Accordingly, Dbait molecules may also be a double stranded molecule with two free ends and having the nucleotide sequence of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5).

In another particular embodiment, they contain only one free end. Preferably, Dbait molecules are made of hairpin nucleic acids with a double-stranded DNA stem and a loop. The loop can be a nucleic acid, or other chemical groups known by a skilled person or a mixture thereof. A nucleotide linker may include from 2 to 10 nucleotides, preferably, 3, 4 or 5 nucleotides. Non-nucleotide linkers non exhaustively include abasic nucleotide, polyether, polyamine, polyamide, peptide, carbohydrate, lipid, polyhydrocarbon, or other polymeric compounds (e. g. oligoethylene glycols such as those having between 2 and 10 ethylene glycol units, preferably 4, 5, 6, 7 or 8 ethylene glycol units). A preferred linker is selected from the group consisting of hexaethyleneglycol, tetradeoxythymidylate (T4), 1,19-bis(phospho)-8-hydraza-2-hydroxy-4-oxa-9-oxo-nonadecane and other linkers such as 2,19-bis(phosphor)-8-hydraza-1-hydroxy-4-oxa-9-oxo-nonadecane. Accordingly, in a particular embodiment, the Dbait molecules can be a hairpin molecule having a double stranded portion or stem comprising at least 16, 18, 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5) and a loop being a hexaethyleneglycol linker, a tetradeoxythymidylate linker (T4), 1,19-bis(phospho)-8-hydraza-2-hydroxy-4-oxa-9-oxo-nonadecane or 2,19-bis(phosphor)-8-hydraza-1-hydroxy-4-oxa-9-oxo-nonadecane. In a more particular embodiment, those Dbait molecules can have a double stranded portion consisting in 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5).

Dbait molecules preferably comprise a 2'-deoxynucleotide backbone, and optionally comprise one or several (2, 3, 4, 5 or 6) modified nucleotides and/or nucleobases other than adenine, cytosine, guanine and thymine. Accordingly, the Dbait molecules are essentially a DNA structure. In particular, the double-strand portion or stem of the Dbait molecules is made of deoxyribonucleotides.

Preferred Dbait molecules comprise one or several chemically modified nucleotide(s) or group(s) at the end of one or of each strand, in particular in order to protect them from degradation. In a particular preferred embodiment, the free end(s) of the Dbait molecules is(are) protected by one, two or three modified phosphodiester backbones at the end of one or of each strand. Preferred chemical groups, in particular the modified phosphodiester backbone, comprise phosphorothioates. Alternatively, preferred Dbait have 3'-3' nucleotide linkage, or nucleotides with methylphosphonate backbone. Other modified backbones are well known in the art and comprise phosphoramidates, morpholino nucleic acid, 2'-0,4'-C methylene/ethylene bridged locked nucleic acid, peptide nucleic acid (PNA), and short chain alkyl, or cycloalkyl intersugar linkages or short chain heteroatomic or heterocyclic intrasugar linkages of variable length, or any modified nucleotides known by a skilled person. In a first preferred embodiment, the Dbait molecules have the free end(s) protected by one, two or three modified phosphodiester backbones at the end of one or of each strand, more preferably by three modified phosphodiester backbones (in particular phosphorothioate or methylphosphonate) at least at the 3'end, but still more preferably at both 5' and 3' ends.

In a most preferred embodiment, the Dbait molecule is a hairpin nucleic acid molecule comprising a DNA double-stranded portion or stem of 32 bp (e.g., with a sequence selected from the group consisting of SEQ ID Nos 1-5, in particular SEQ ID No 4) and a loop linking the two strands of the DNA double-stranded portion or stem comprising or consisting of a linker selected from the group consisting of hexaethyleneglycol, tetradeoxythymidylate (T4), 1,19-bis(phospho)-8-hydraza-2-hydroxy-4-oxa-9-oxo-nonadecane and 2,19-bis(phosphor)-8-hydraza-1-hydroxy-4-oxa-9-oxo-nonadecane, the free ends of the DNA double-stranded portion or stem (i.e. at the opposite of the loop) having three modified phosphodiester backbones (in particular phosphorothioate internucleotidic links).

Said nucleic acid molecules are made by chemical synthesis, semi-biosynthesis or biosynthesis, any method of amplification, followed by any extraction and preparation methods and any chemical modification. Linkers are provided so as to be incorporable by standard nucleic acid chemical synthesis.

More preferably, nucleic acid molecules are manufactured by specially designed convergent synthesis: two complementary strands are prepared by standard nucleic acid chemical synthesis with the incorporation of appropriate linker precursor, after their purification, they are covalently coupled together.

Optionally, the nucleic acid molecules may be conjugated to molecules facilitating endocytosis or cellular uptake.

In particular, the molecules facilitating endocytosis or cellular uptake may be lipophilic molecules such as cholesterol, single or double chain fatty acids, or ligands which target cell receptor enabling receptor mediated endocytosis, such as folic acid and folate derivatives or transferrin (Goldstein et al. Ann. Rev. Cell Biol. 1985 1:1-39; Leamon & Lowe, Proc Natl Acad Sci USA. 1991, 88: 5572-5576). The molecule may also be tocopherol, sugar such as galactose and mannose and their oligosaccharide, peptide such as RGD and bombesin and protein such as integrin. Fatty acids may be saturated or unsaturated and be in C4-C28, preferably in C14-C22, still more preferably being in C18 such as oleic acid or stearic acid. In particular, fatty acids may be octadecyl or dioleoyl. Fatty acids may be found as double chain form linked with an appropriate linker such as a glycerol, a phosphatidylcholine or ethanolamine and the like or linked together by the linkers used to attach on the Dbait molecule. As used herein, the term "folate" is meant to refer to folate and folate derivatives, including pteroic acid derivatives and analogs. The analogs and derivatives of folic acid suitable for use in the present invention include, but are not limited to, antifolates, dihydrofolates, tetrahydrofolates, folinic acid, pteropolyglutamic acid, 1-deza, 3-deaza, 5-deaza, 8-deaza, 10-deaza, 1,5-deaza, 5,10 dideaza, 8,10-dideaza, and 5,8-dideaza folates, and pteroic acid derivatives. Additional folate analogs are described in US2004/242582. Accordingly, the molecule facilitating endocytosis may be selected from the group consisting of single or double chain fatty acids, folates and cholesterol. More preferably, the molecule facilitating endocytosis is selected from the group consisting of dioleoyl, octadecyl, folic acid, and cholesterol. In a most preferred embodiment, the nucleic acid molecule is conjugated to a cholesterol.

The molecules facilitating endocytosis are conjugated to Dbait molecules, preferably through a linker. Any linker known in the art may be used to covalently attach the molecule facilitating endocytosis to Dbait molecules. For instance, WO09/126933 provides a broad review of convenient linkers pages 38-45. The linker can be non-exhaustively, aliphatic chain, polyether, polyamine, polyamide, peptide, carbohydrate, lipid, polyhydrocarbon, or other polymeric compounds (e. g. oligoethylene glycols such as those having between 2 and 10 ethylene glycol units, preferably 3, 4, 5, 6, 7 or 8 ethylene glycol units, still more preferably 6 ethylene glycol units), as well as incorporating any bonds that may break down by chemical or enzymatical way, such as a disulfide linkage, a protected disulfide linkage, an acid labile linkage (e.g., hydrazone linkage), an ester linkage, an ortho ester linkage, a phosphonamide linkage, a biocleavable peptide linkage, an azo linkage or an aldehyde linkage. Such cleavable linkers are detailed in WO2007/040469 pages 12-14, in WO2008/022309 pages 22-28.

In a particular embodiment, the nucleic acid molecule can be linked to one molecule facilitating endocytosis. Alternatively, several molecules facilitating endocytosis (e.g., two, three or four) can be attached to one nucleic acid molecule.

In a specific embodiment, the linker between the molecule facilitating endocytosis, in particular cholesterol, and nucleic acid molecule is CO—NH—($CH_2$—$CH_2$—O)$_n$, wherein n is an integer from 1 to 10, preferably n being selected from the group consisting of 3, 4, 5 and 6. In a very particular embodiment, the linker is CO—NH—($CH_2$—$CH_2$—O)$_4$ (carboxamido tetraethylene glycol). In another very particular embodiment, the linker is CO—NH—($CH_2$—$CH_2$—O)$_3$ (carboxamido triethylene glycol). The linker can be linked to nucleic acid molecules at any convenient position which does not modify the activity of the nucleic acid molecules. In particular, the linker can be linked at the 5' end, at the 3' end or in the loop when the nucleic acid molecule is a hairpin. Therefore, in a preferred embodiment, the contemplated conjugated Dbait molecule is a Dbait molecule having a hairpin structure and being conjugated to the molecule facilitating endocytosis, preferably through a linker, at its 5' end.

In another specific embodiment, the linker between the molecule facilitating endocytosis, in particular cholesterol, and nucleic acid molecule is dialkyl-disulfide {e.g., ($CH_2$)r-S—S—($CH_2$)s with r and s being an integer from 1 to 10, preferably from 3 to 8, for instance 6}.

In a most preferred embodiment, the conjugated Dbait molecule is a hairpin nucleic acid molecule comprising a DNA double-stranded portion or stem of 32 bp (e.g., with a sequence selected from the group consisting of SEQ ID Nos 1-5, in particular SEQ ID No 4) and a loop linking the two strands of the DNA double-stranded portion or stem comprising or consisting of a linker selected from the group consisting of hexaethyleneglycol, tetradeoxythymidylate (T4), 1,19-bis(phospho)-8-hydraza-2-hydroxy-4-oxa-9-oxo-nonadecane and 2,19-bis(phosphor)-8-hydraza-1-hydroxy-4-oxa-9-oxo-nonadecane, the free ends of the DNA double-stranded portion or stem (i.e. at the opposite of the loop) having three modified phosphodiester backbones (in particular phosphorothioate internucleotidic links) and said Dbait molecule being conjugated to a cholesterol at its 5' end, preferably through a linker (e.g. carboxamido oligoethylene glycol, preferably carboxamido triethylene glycol or carboxamido tetraethylene glycol).

In a preferred embodiment, NNNN—(N)$_n$—N comprises at least 6, 8, 10, 12, 14, 16, 18, 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5) or consists in 20, 22, 24, 26, 28, 30 or 32 consecutive nucleotides of Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5). In a particular embodiment, NNNN—(N)$_n$—N comprises or consists in Dbait32 (SEQ ID No 1), Dbait32Ha (SEQ ID No 2), Dbait32Hb (SEQ ID No 3), Dbait32Hc (SEQ ID No 4) or Dbait32Hd (SEQ ID No 5), more preferably Dbait32Hc (SEQ ID No 4).

Accordingly, the conjugated Dbait molecule or hairpin nucleic acid molecule may be selected from the group consisting of:

with NNNN—(N)$_n$—N being SEQ ID No 1

(Ia) SEQ ID No 6

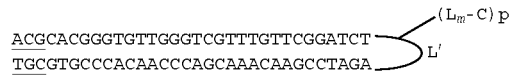

(IIa) SEQ ID No 11

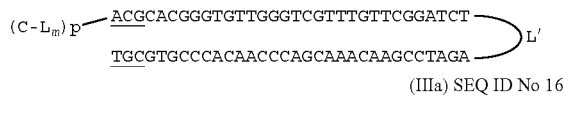

(IIIa) SEQ ID No 16

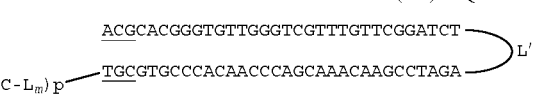

with NNNN—(N)$_n$—N being SEQ ID No 2

(Ib) SEQ ID No 7

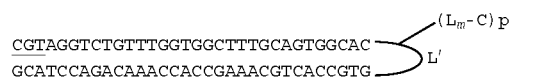

(IIb) SEQ ID No 12

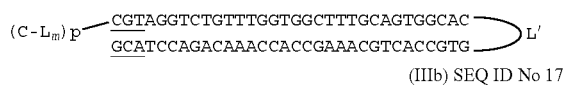

(IIIb) SEQ ID No 17

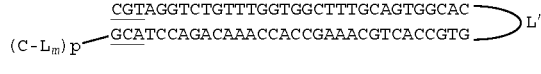

-continued with NNNN—(N)ₙ—N being SEQ ID No 3

(Ic) SEQ ID No 8

```
GCTAGGCTTGTTTGCTGGGTTGTAGGCACAGC ⎫        (Lₘ-C)p
CGATCCGAACAAACGACCCAACATCCGTGTCG ⎭ L'
```

(IIc) SEQ ID No 13

```
            GCTAGGCTTGTTTGCTGGGTTGTAGGCACAGC ⎫
(C-Lₘ)p—    CGATCCGAACAAACGACCCAACATCCGTGTCG ⎭ L'
```

(IIIc) SEQ ID No 18

```
            GCTAGGCTTGTTTGCTGGGTTGTAGGCACAGC ⎫
(C-Lₘ)p—    CGATCCGAACAAACGACCCAACATCCGTGTCG ⎭ L'
``` with NNNN—(N)ₙ—N being SEQ ID No 4

(Id) SEQ ID No 9

```
GCTGTGCCCACAACCCAGCAAACAAGCCTAGA ⎫        (Lₘ-C)p
CGACACGGGTGTTGGGTCGTTTGTTCGGATCT ⎭ L'
```

SEQ ID No 14

```
            GCTGTGCCCACAACCCAGCAAACAAGCCTAGA ⎫
(C-Lₘ)p—    CGACACGGGTGTTGGGTCGTTTGTTCGGATCT ⎭ L'
```

(IId) SEQ ID No 22

(IIId) SEQ ID No 19

```
            GCTGTGCCCACAACCCAGCAAACAAGCCTAGA ⎫
(C-Lₘ)p—    CGACACGGGTGTTGGGTCGTTTGTTCGGATCT ⎭ L'
``` with NNNN—(N)ₙ—N being SEQ ID No 5

(Ie) SEQ ID No 10

```
GCTAGGTCTGTTTGGTGGCTTTGCAGTGGCAC ⎫        Lₘ-C
CGATCCAGACAAACCACCGAAACGTCACCGTG ⎭ L'
```

(IIe) SEQ ID No 15

```
        GCTAGGTCTGTTTGGTGGCTTTGCAGTGGCAC ⎫
C-Lₘ—   CGATCCAGACAAACCACCGAAACGTCACCGTG ⎭ L' and,
```

(IIIe) SEQ ID No 20

```
        GCTAGGTCTGTTTGGTGGCTTTGCAGTGGCAC ⎫
C-Lₘ—   CGATCCAGACAAACCACCGAAACGTCACCGTG ⎭ L'
``` with the same definition than formulae (I), (II) and (III) for L, L', C, p and m.

In preferred embodiments, the molecule of formulae (Ia), (IIa), (IIIa), (Ib), (IIb), (IIIb), (Ic), (IIc), (IIIc), (Id), (IId), (IIId), (Ie), (IIe) and (IIIe), preferably of formulae (II), (IIa), (IIb), (IIc), (IId) and (IIe), has one or several of the following features:

the underlined nucleotide refers to a nucleotide having or not a phosphorothioate or methylphosphonate backbone, more preferably a phosphorothioate backbone; preferably, the underlined nucleotide refers to a nucleotide having a phosphorothioate or methylphosphonate backbone, more preferably a phosphorothioate backbone; and/or, the linked L' is selected from the group consisting of hexaethyleneglycol, tetradeoxythymidylate (T4), 1,19-bis(phospho)-8-hydraza-2-hydroxy-4-oxa-9-oxo-nonadecane and 2,19-bis(phosphor)-8-hydraza-1-hydroxy-4-oxa-9-oxo-nonadecane; and/or, m is 1 and L is a carboxamido polyethylene glycol, more preferably carboxamido triethylene glycol or carboxamido tetraethylene glycol; and/or, p is 1; and/or, C is selected from the group consisting of a cholesterol, single or double chain fatty acids such as octadecyl, oleic acid, dioleoyl or stearic acid, or ligand (including peptide, protein, aptamer) which targets cell receptor such as folic acid, tocopherol, sugar such as galactose and mannose and their oligosaccharide, peptide such as RGD and bombesin, and protein such transferring and integrin, preferably is a cholesterol.

Preferably, C-Lm is a triethyleneglycol linker (10-O-[1-propyl-3-N-carbamoylcholesteryl]-triethyleneglycol radical. Alternatively, C-Lm is a tetraethyleneglycol linker (10-O-[1-propyl-3-N-carbamoylcholesteryl]-tetraethyleneglycol radical.

In a specific embodiment of the Dbait molecules or hairpin nucleic acid molecules of formulae (I), (II), (II'), (III), (Ia), (IIa), (IIIa), (Ib), (IIb), (IIIb), (Ic), (IIc), (IIIc), (Id), (IId), (IIId), (Ie), (IIe) and (IIIe), preferably of formulae (II), (II'), (IIa), (IIb), (IIc), (IId) and (IIe), L' is preferably selected from the group consisting of hexaethyleneglycol, tetradeoxythymidylate (T4), 1,19-bis(phospho)-8-hydraza-2-hydroxy-4-oxa-9-oxo-nonadecane and 2,19-bis(phosphor)-8-hydraza-1-hydroxy-4-oxa-9-oxo-nonadecane.

In a specific embodiment of the Dbait molecules or hairpin nucleic acid molecules of formulae (I), (II), (II'), (III), (Ia), (IIa), (IIIa), (Ib), (IIb), (IIIb), (Ic), (IIc), (IIIc), (Id), (IId), (IIId), (Ie), (IIe) and (IIIe), preferably of formulae (II), (II'), (IIa), (IIb), (IIc), (IId) and (IIe), with C being cholesterol, C-$L_m$ is the radical In a preferred embodiment, the conjugated Dbait molecule or hairpin nucleic acid molecule is selected from the group consisting of (II), (II'), (IIa), (IIb), (IIc), (IId), and (IIe), wherein $C-L_m$ being the radical

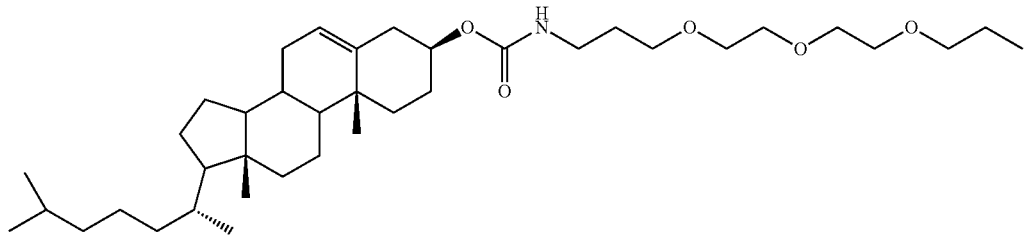 [SMILES: CCCOCCOCCOCCCNC(=O)O[C@H]1CC[C@@]2(C)C(=CCC3C4CCC([C@H](C)CCCC(C)C)[C@@]4(C)CCC32)C1]

and wherein L' is preferably selected from the group consisting of hexaethyleneglycol, tetradeoxythymidylate (T4), 1,19-bis(phospho)-8-hydraza-2-hydroxy-4-oxa-9-oxo-nonadecane and 2,19-bis(phosphor)-8-hydraza-1-hydroxy-4-oxa-9-oxo-nonadecane, more preferably 2,19-bis(phosphor)-8-hydraza-1-hydroxy-4-oxa-9-oxo-nonadecane.

In a very specific embodiment, the Dbait molecule or hairpin nucleic acid molecule has the following formula SEQ ID No 14

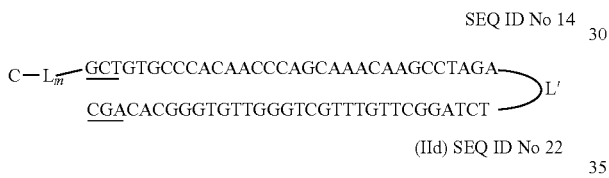

(IId) SEQ ID No 22 wherein $C-L_m$ is the radical

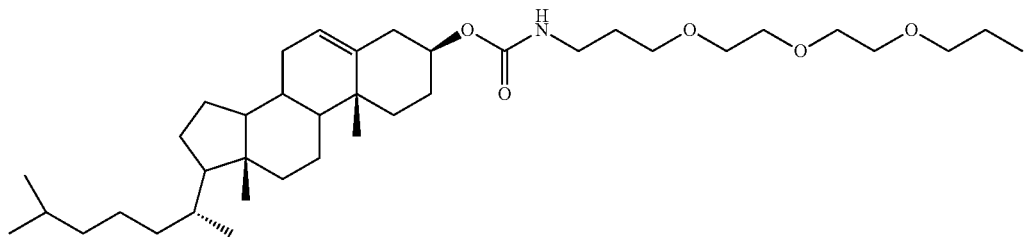

wherein L' is 2,19-bis(phosphor)-8-hydraza-1-hydroxy-4-oxa-9-oxo-nonadecane and wherein the underlined nucleotides have a phosphorothioate backbone. Accordingly, the molecule has the following structure and it is referred thereto in the Example section as "coDbait".

SEQ ID No 21

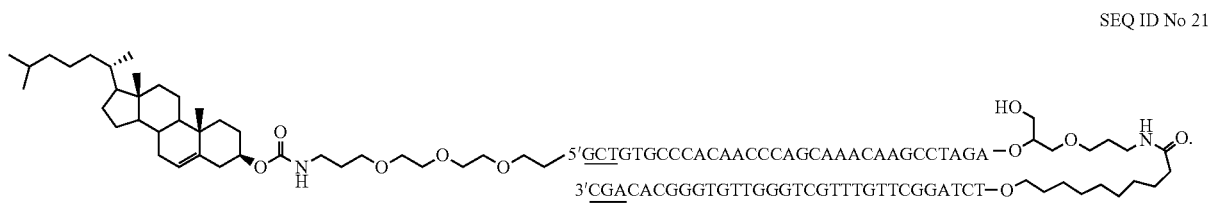 [SMILES: CCCOCCOCCOCCCNC(=O)O[C@@H]1CC[C@]2(C)C(=CCC3C4CCC([C@@H](C)CCCC(C)C)[C@]4(C)CCC32)C1 ; COCCCCCCCCCC(=O)NCCCOCC(CO)OC]

In a specific embodiment of the Dbait molecules or hairpin nucleic acid molecules of formulae (I), (II), (II'), (III), (Ia), (IIa), (IIIa), (Ib), (IIb), (IIIb), (Ic), (IIc), (IIIc), (Id), (IId), (IIId), (Ie), (IIe) and (IIIe), preferably of formulae (II), (II'), (IIa), (IIb), (IIc), (IId) and (IIe), with C being cholesterol, C-$L_m$ is a tetraethyleneglycol linker (10-O-[1-propyl-3-N-carbamoylcholesteryl]-tetraethyleneglycol radical.

In a preferred embodiment, the conjugated Dbait molecule or hairpin nucleic acid molecule is selected from the group consisting of (II), (II'), (IIa), (IIb), (IIc), (IId), and (IIe), wherein C-$L_m$ being the tetraethyleneglycol linker (10-O-[1-propyl-3-N-carbamoylcholesteryl]-tetraethyleneglycol radical and wherein L' is preferably selected from the group consisting of hexaethyleneglycol, tetradeoxythymidylate (T4), 1,19-bis(phospho)-8-hydraza-2-hydroxy-4-oxa-9-oxo-nonadecane and 2,19-bis(phosphor)-8-hydraza-1-hydroxy-4-oxa-9-oxo-nonadecane, more preferably 1,19-bis(phospho)-8-hydraza-2-hydroxy-4-oxa-9-oxo-nonadecane.

In a very specific embodiment, the Dbait molecule or hairpin nucleic acid molecule (AsiDNA or DT01) has the following formula

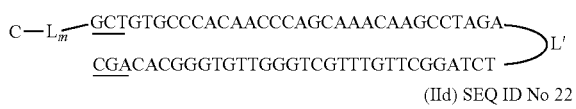

wherein C-$L_m$ is the tetraethyleneglycol linker (10-O-[1-propyl-3-N-carbamoylcholesteryl]-tetraethyleneglycol radical, and L' is 1,19-bis(phospho)-8-hydraza-2-hydroxy-4-oxa-9-oxo-nonadecane.

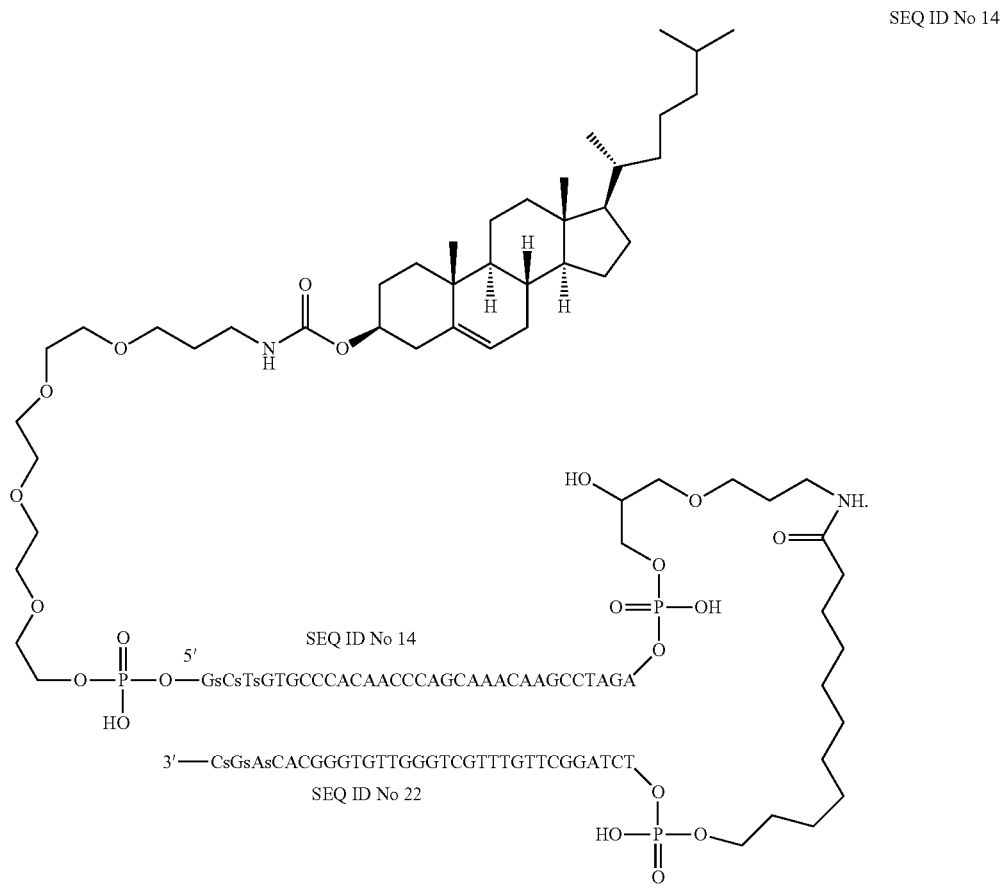

In another preferred embodiment, the nucleic acid molecule has one of the following formulae

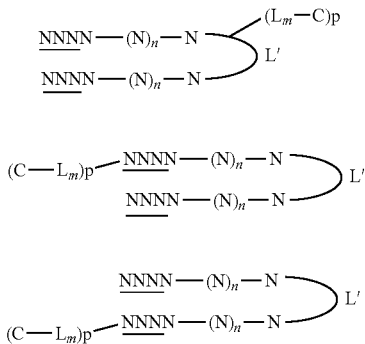

wherein N is a deoxynucleotide, n is an integer from 1 to 15, the underlined N refers to a nucleotide having or not a modified phosphodiester backbone, L' is a linker, C is a cholesterol, L is a linker, m is an integer being 0 or 1, and p is 1. Preferably, the underlined N refers to a nucleotide having a modified phosphodiester backbone. In a preferred embodiment, the nucleic acid molecule as the formula (II).

Accordingly, the present invention also relates the use of a Dbait molecule or a nucleic acid molecule as disclosed above, a pharmaceutical composition comprising it and optionally a pharmaceutically acceptable carrier, for use in the treatment of cancer in combination with a PARP inhibitor, and with or without radiotherapy and/or radioisotope therapy and/or an antitumor chemotherapy, preferably with a DNA damaging antitumoral agent, as detailed below.
Further Combinations Optionally, the treatment with a nucleic acid molecule as disclosed herein and a PARP inhibitor can be used in combination with a radiotherapy, a radioisotope therapy and/or another antitumor chemotherapy, immunotherapy, or hormonal therapy. Preferably, the antitumor chemotherapy is a treatment by a DNA damaging antitumor agent, either directly or indirectly.

As used herein, the term "antitumor chemotherapy" or "chemotherapy" refers to a cancer therapeutic treatment using chemical or biochemical substances, in particular using one or several antineoplastic agents. In particular, it also includes hormonal therapy and immunotherapy. The term "hormonal therapy" refers to a cancer treatment having for purpose to block, add or remove hormones. For instance, in breast cancer, the female hormones estrogen and progesterone can promote the growth of some breast cancer cells. So in these patients, hormone therapy is given to block estrogen and a non-exhaustive list commonly used drugs includes: Tamoxifen, Fareston, Arimidex, Aromasin, Femara, Zoladex/Lupron, Megace, and Halotestin. The term "immunotherapy" refers to a cancer therapeutic treatment using the immune system to reject cancer. The therapeutic treatment stimulates the patient's immune system to attack the malignant tumor cells.

In a particular aspect, the nucleic acid molecule as disclosed herein and PARP inhibitor are used in combination with a DNA-damaging treatment. The DNA-damaging treatment can be radiotherapy, or chemotherapy with a DNA-damaging antitumoral agent, or a combination thereof. DNA-damaging treatment refers to a treatment inducing DNA strand breakage, preferably relatively specifically in cancer cells.

DNA strand breakage can be achieved by ionized radiation (radiotherapy). Radiotherapy includes, but is not limited to, γ-rays, X-rays, and/or the directed delivery of radioisotopes to tumor cells. Other radiotherapies include microwaves and UV-irradiation. Other approaches to radiation therapy are also contemplated in the present invention.

DNA strand breakage can be achieved by radioisotope therapy, in particular by administration of a radioisotope, preferably a targeted radioisotope. Targeting can be due to the chemical properties of the isotope such as radioiodine which is specifically absorbed by the thyroid gland a thousand fold better than other organs. Alternatively, the targeting can be achieved by attaching to the radioisotope another molecule having targeting properties such hapten or antibody. Any of a number of suitable radioactive isotopes can be used, including, but not limited to, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-ill, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211.

The DNA-damaging antitumor agent is preferably selected from the group consisting of an inhibitor of topoisomerases I or II, a DNA crosslinker, a DNA alkylating agent, an anti-metabolic agent and inhibitors of the mitotic spindles.

Inhibitors of topoisomerases I and/or II include, but are not limited to, etoposide, topotecan, camptothecin, irinotecan, amsacrine, intoplicine, anthracyclines such as doxorubicine, epirubicine, daunorubicine, idanrubicine and mitoxantrone. Inhibitors of Topoisomerase I and II include, but are not limited to, intoplecin.

DNA crosslinkers include, but are not limited to, cisplatin, carboplatin and oxaliplatin.

Anti-metabolic agents block the enzymes responsible for nucleic acid synthesis or become incorporated into DNA, which produces an incorrect genetic code and leads to apoptosis. Non-exhaustive examples thereof include, without limitation, folic acid antagonists, pyrimidine analogs, purine analogs and adenosine deaminase inhibitors, and more particularly Methotrexate, Floxuridine, Cytarabine, 6-Mercaptopurine, 6-Thioguanine, Fludarabine phosphate, Pentostatine, 5-fluorouracil, gemcitabine and capecitabine.

The DNA-damaging anti-tumoral agent can be alkylating agents including, without limitation, nitrogen mustards, ethylenimine derivatives, alkyl sulfonates, nitrosoureas, metal salts and triazenes. Non-exhaustive examples thereof include Uracil mustard, Chlormethine, Cyclophosphamide (CYTOXAN®), Ifosfamide, Melphalan, Chlorambucil, Pipobroman, Triethylenemelamine, Triethylenethiophosphoramine, Busulfan, Carmustine, Lomustine, Fotemustine, cisplatin, carboplatin, oxaliplatin, thiotepa, Streptozocin, Dacarbazine, and Temozolomide.

Inhibitors of the mitotic spindles include, but are not limited to, paclitaxel, docetaxel, vinorelbine, larotaxel (also called XRP9881; Sanofi-Aventis), XRP6258 (Sanofi-Aventis), BMS-184476 (Bristol-Meyer-Squibb), BMS-188797 (Bristol-Meyer-Squibb), BMS-275183 (Bristol-Meyer-Squibb), ortataxel (also called IDN 5109, BAY 59-8862 or SB-T-101131; Bristol-Meyer-Squibb), RPR 109881A (Bristol-Meyer-Squibb), RPR 116258 (Bristol-Meyer-Squibb), NBT-287 (TAPESTRY), PG-paclitaxel (also called CT-2103, PPX, paclitaxel poliglumex, paclitaxel polyglutamate or Xyotax™), ABRAXANE® (also called Nab-Paclitaxel; ABRAXIS BIOSCIENCE), Tesetaxel (also called DJ-927), IDN 5390 (INDENA), Taxoprexin (also called docosahexanoic acid-paclitaxel; PROTARGA), DHA-paclitaxel (also called Taxoprexin®), and MAC-321 (WYETH). Also see the review of Hennenfent & Govindan (2006, *Annals of Oncology*, 17, 735-749).

Cancers or Tumors to be Treated

The terms "cancer", "cancerous", or "malignant" refer to or describe the physiological condition in mammals that is typically characterized by unregulated cell growth. Examples of cancer include, for example, leukemia, lymphoma, blastoma, carcinoma and sarcoma.

More particular examples of such cancers include chronic myeloid leukemia, acute lymphoblastic leukemia, Philadelphia chromosome positive acute lymphoblastic leukemia (Ph+ ALL), squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatocarcinoma, breast cancer, colon carcinoma, and head and neck cancer, gastric cancer, germ cell tumor, pediatric sarcoma, multiple myeloma, acute myelogenous leukemia (AML), chronic lymphocytic leukemia, mastocytosis and any symptom associated with mastocytosis.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocyte leukemia, micromyeloblastic leukemia, monocytic leukemia, myeloblasts leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia. In certain aspects, the present invention provides treatment for chronic myeloid leukemia, acute lymphoblastic leukemia, and/or Philadelphia chromosome positive acute lymphoblastic leukemia (Ph+ ALL).

Various cancers are also encompassed by the scope of the invention, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testis, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyosarcoma, and osteosarcoma; other tumors including melanoma, xenoderma pigmentosum, keratoactanthoma, seminoma, thyroid follicular cancer, and teratocarcinoma; melanoma, unresectable stage III or IV malignant melanoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, hepatocarcinoma, breast cancer, colon carcinoma, and head and neck cancer, retinoblastoma, gastric cancer, germ cell tumor, bone cancer, bone tumors, adult malignant fibrous histiocytoma of bone; childhood malignant fibrous histiocytoma of bone, sarcoma, pediatric sarcoma; myelodysplastic syndromes; neuroblastoma; testicular germ cell tumor, intraocular melanoma, myelodysplastic syndromes; myelodysplastic/myeloproliferative diseases, synovial sarcoma.

In a preferred embodiment of the present invention, the cancer is a solid tumor. For instance, the cancer may be sarcoma and osteosarcoma such as Kaposi sarcoma, AIDS-related Kaposi sarcoma, melanoma, in particular ulveal melanoma, and cancers of the head and neck, kidney, ovary, pancreas, prostate, thyroid, lung, esophagus, breast, bladder, colorectum, liver and biliary tract, uterine, appendix, and cervix, testicular cancer, gastrointestinal cancers and endometrial and peritoneal cancers. Preferably, the cancer may be sarcoma, melanoma, in particular ulveal melanoma, and cancers of the head a neck, kidney, ovary, pancreas, prostate, thyroid, lung, esophagus, breast, bladder, colorectum, liver, cervix, and endometrial and peritoneal cancers.

The pharmaceutical compositions and the products, kits or combined preparations described in the invention may be useful for inhibiting the growth of solid tumors, decreasing the tumor volume, preventing the metastatic spread of tumors and the growth or development of micrometastases. The pharmaceutical compositions and the products, kits or combined preparations described in the invention are in particular suitable for the treatment of poor prognosis patients or of radio- or chemo-resistant tumors.

In a particular embodiment, the cancer is a high-grade or advanced cancer or is a metastatic cancer.

In another particular embodiment, the cancer is not deficient or impaired for the homologous recombination repair (e.g., not BRCA mutated nor BRCAness).

Regimen, Dosages and Administration Routes

The effective dosage of each of the combination partners employed in the combined preparation of the invention may vary depending on the particular compound or pharmaceutical composition employed, the mode of administration, the condition being treated, the severity of the condition being treated. Thus, the dosage regimen of the combined preparation of the invention is selected in accordance with a variety of factors including the route of administration and the patient status. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

The present invention more particularly relates to a pharmaceutical composition, a kit, product or combined preparation wherein the amount or dosage of the PARP inhibitor can be lowered in comparison with its amount or dosage when it is used alone. Indeed, the combination of a Dbait molecule and a PARP inhibitor leads at least to an additive effect but rather to a clear synergistic effect of the two active ingredients This potentiating effect allows the decrease of the amount of the PARP inhibitor, which generally exhibit a toxicity for the normal cells and therefore can be associated with adverse effects. The Dbait molecules advantageously exhibit a minimal toxicity, and even no toxicity. Then, with the combined treatment of the invention, it is possible to preserve the efficacy of the treatment, or even to improve it, while decreasing its adverse effects, in particular the adverse effects of the PARP inhibitor.

Alternatively, instead of lowering the amount or dosage of the PARP inhibitor, the administration frequency of the PARP inhibitor or its or treatment period can be reduced.

According to an embodiment, the present invention relates to a method for the treatment of a cancer, to a pharmaceutical composition, to a product, kit or combined preparation as disclosed above, wherein the amounts of the nucleic acid molecule as disclosed herein and the PARP inhibitor in the combined preparation are such that the combined therapeutic effect of the two active ingredients is additional or preferably synergistic.

By the term "synergistic" therapeutic effect is meant that the obtained therapeutic effect of the combination is more than the addition of the therapeutic effect of each partner alone (i.e. more than the effect of the nucleic acid molecule as disclosed herein alone plus the effect of the PARP inhibitor alone).

By the term "additional" therapeutic effect is meant that the obtained therapeutic effect of the combination is the addition of the therapeutic effect of each partner alone (i.e. equals to the effect of the nucleic acid molecule as disclosed herein alone plus the effect of the PARP inhibitor alone).

The present invention relates to a method for the treatment of a cancer, to a pharmaceutical composition, to a product, kit or combined preparation as disclosed above, wherein the PARP inhibitor is used at lower dosage than the conventional dosage used in chemotherapy for the same indication and the same administration route when it is used alone (i.e., an amount equal to or preferably lower than the one used in conventional chemotherapy), also called herein a sub-therapeutic amount. More particularly, the amount can be for instance 90, 80, 70, 60, 50, 40, 30, 20 or 10% of the conventional therapeutic dosage (in particular for the same indication and the same administration route). The conventional therapeutic dosages are those acknowledged by the drug approvals agencies (e.g., FDA or EMEA). In that respect, the present invention relates to a method for the treatment of a cancer, to a pharmaceutical composition, to a product, kit or combined preparation as disclosed above, wherein the amount of the PARP inhibitor is used at a sub-therapeutic dosage and the amount of nucleic acid molecule as disclosed herein is such that the combined therapeutic effect of the two active ingredients is additional or more preferably synergistic.

The present invention relates to a method for the treatment of a cancer comprising administering a synergistically therapeutically effective amount of the combined preparation of (a) a nucleic acid molecule as disclosed herein and (b) a PARP inhibitor.

The invention also relates to a synergistic combination which comprises (a) a nucleic acid molecule as disclosed herein and (b) a PARP inhibitor in a synergistic ratio for simultaneous, separate or sequential use, in particular in the treatment of cancer.

In a particular embodiment, the nucleic acid molecule as disclosed herein is DT01 as defined above and the PARP inhibitor is selected among the group consisting of AZD2281 (Olaparib), ABT888 (Veliparib), BMN673, BSI-21 (Iniparib), AZD 2461, MK-4827 (Niraparib), and AG 014699 (Rucaparib), more preferably is AZD2281 (Olaparib) or ABT888 (Veliparib).

By the term "synergistically therapeutically effective amount" or "synergistic ratio" is meant that the therapeutic effect of the combination is more than the addition of the therapeutic effect of each partner alone (i.e. more than the therapeutic effect of the nucleic acid molecule as disclosed herein alone plus the therapeutic effect of the PARP inhibitor alone).

The invention also relates to a pharmaceutical composition comprising a quantity which is jointly therapeutically effective against a cancer of the combination of the invention and at least one pharmaceutically acceptable carrier.

In a particular embodiment of the invention, the synergistic combination is such that the PARP inhibitor is used or administered in a sub-therapeutic amount. In particular, a sub-therapeutic amount of the PARP inhibitor is less than the conventional dosage used to treat a cancer as a single drug (i.e., not in combination with another drug). More particularly, the sub-therapeutic amount can be for instance 90, 80, 70, 60, 50, 40, 30, 20 or 10% of the conventional therapeutic dosage for the same indication and the same administration route. The conventional therapeutic dosages are those acknowledged by the drug approvals agencies (e.g., FDA or EMEA) and can be found in reference.

Determining an additional or a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in one species can be predictive of the effect in other species and animal models exist to measure a synergistic effect and the results of such studies can also be used to predict effective dose and plasma concentration ratio ranges and the absolute doses and plasma concentrations required in other species by the application of pharmacokinetic/pharmacodynamic methods. Correlations between cancer models and effects seen in man suggest that observed synergy on animal models may be predictive of a synergy on man too.

The pharmacological activity of a combination of the invention may, for example, be demonstrated in a clinical study or more preferably in a test procedure. Suitable clinical studies are, for example, open label non-randomized, dose escalation studies in patients with advanced tumors. Such studies can prove the additive or synergism of the active ingredients of the combination of the invention. The beneficial effects on proliferative diseases can be determined directly through the results of these studies or by changes in the study design which are known as such to a person skilled in the art. Such studies are, in particular, suitable to compare the effects of a monotherapy using the active ingredients and a combination of the invention. Preferably, the combination partner (a) is administered with a fixed dose and the dose of the combination partner (b) is escalated until the maximum tolerated dosage is reached. Alternatively, the combination partner (b) is administered with a fixed dose and the dose of the combination partner (a) is escalated until the maximum tolerated dosage is reached.

The administration route for nucleic acid molecule as disclosed herein may be oral, parental, intravenous, intratumoral, subcutaneous, intracranial, intra-artery, topical, rectal, transdermal, intradermal, nasal, intramuscular, intraperitoneal, intraosseous, and the like. In a preferred embodiment, the Dbait molecules are to be administered or injected near the tumoral site(s) to be treated. In a further particular embodiment, when the cancer to be treated is a melanoma, the nucleic acid molecule as disclosed herein may be delivered by subcutaneous and intravenous injection. Another preferred administration route is an intratumoral injection.

When a DNA-damaging antitumoral agent is used in combination with the nucleic acid molecule as disclosed herein and a PARP inhibitor, the DNA-damaging antitumoral agent, the nucleic acid molecule as disclosed herein and the PARP inhibitor may be administered by the same route or by distinct routes. The administration route for the DNA-damaging antitumoral agent may be oral, parenteral, intravenous, intratumoral, subcutaneous, intracranial, intraartery, topical, rectal, transdermal, intradermal, nasal, intramuscular, intraosseous, and the like.

The nucleic acid molecule as disclosed herein is to be administered before and/or simultaneously with and/or after the irradiation and/or the administration of the DNA-damaging antitumoral agent, more preferably before and/or simultaneously with the irradiation and/or the administration of the DNA-damaging antitumoral agent. The irradiation and/or the administration of the DNA-damaging antitumoral agent is performed so as the nucleic acid molecule as disclosed herein is present in the tumoral cells when the irradiation is applied or when the DNA-damaging antitumoral agent reach the tumoral cells. The physician, clinician or veterinarian of ordinary skill can determine the regimen based on the active ingredients, their kinetics of availability to target sites or their pharmacokinetic profiles in plasma. Preliminary results indicate that Dbait molecules stay active during one day.

Once the treatment by radiotherapy or with the DNA-damaging antitumoral agent has begun, the treatment with the nucleic acid molecule as disclosed herein can continue as long as the treatment by radiotherapy or with the DNA-damaging antitumoral agent is to be applied or administered. Alternatively, the treatment with the nucleic acid molecule as disclosed herein can also end.

The effective dosage of the nucleic acid molecule as disclosed herein employed in combination with a PARP inhibitor may vary depending on the mode of administration, the condition being treated, the severity of the condition being treated. Thus, the dosage regimen of the nucleic acid molecule as disclosed herein is selected in accordance with a variety of factors including the route of administration and the patient status. A physician, clinician or veterinarian of ordinary skill can readily determine and prescribe the effective amount of the nucleic acid molecule as disclosed herein required to prevent, counter or arrest the progress of the cancer.

For instance, for local administration (e.g., when the intratumoral or sub-cutaneous administration is used), the efficient amount of the Dbait molecules is at least 0.01 mg per 1 $cm^3$ of tumor, preferably 0.1-40 mg per 1 $cm^3$ of tumor, most preferably 1-20 mg per 1 $cm^3$ of tumor. The efficient amount can be administered in a daily treatment protocol (e.g., 5 days per week for 3 to 6 consecutive weeks or 3 times a week for 3 to 6 consecutive weeks). Alternatively, an efficient amount of at least 0.1 mg per 1 $cm^3$ of tumor, preferably 0.1-40 mg per 1 $cm^3$ of tumor, most preferably 1-20 mg per 1 $cm^3$ of tumor, can be administered in a weekly treatment protocol for 3-6 consecutive weeks, for instance. When other administration routes are used, the one skilled in the art can adapt the amount in order to obtain an efficient amount of the Dbait molecules in the tumor of at least 0.01 mg per 1 $cm^3$ of tumor, preferably 0.1-40 mg per 1 $cm^3$ of tumor, most preferably 1-20 mg per 1 $cm^3$ of tumor, in particular in a daily treatment protocol or in a weekly treatment protocol. For instance, for a systemic route, the efficient amount or unit dosage of the Dbait molecules may be of 0.1 to 100 mg, preferably of 4 to 40 mg. Accordingly, for a systemic route, the efficient amount or unit dosage of the Dbait molecules may be of 0.06 to 0.6 mg/kg of patient. Of course, the dosage and the regimen can be adapted by the one skilled in art in consideration of the chemotherapy and/or radiotherapy regimen. For radiotherapy, any radiotherapy regimen known in the art may be used, in particular stereotactic irradiation (e.g., 15 Gy) or a fractionated irradiation. The use of a fractionated irradiation may be particularly efficient, for instance irradiation may applied every day or every 2-5 days, preferably every 3-4 days, in a period of one, two, three, four, five or six weeks. The irradiation may be from 1 to 10 Gy, preferably from 2 to 5 Gy, in particular 2, 3, 4 or 5 Gy. For instance, fractionated irradiation of 15×2Gy in six weeks, or of 4 to 6×5Gy in two weeks may be contemplated. In a preferred embodiment, the contemplated radiotherapy is a protocol with 4 irradiations of 5 Gy in two weeks. Different regimens or conditions of combined treatments of cancer with irradiation and Dbait molecules have been tested and allowed to demonstrate the radio-sentization of tumors by Dbait molecules depends on the doses of Dbait molecules but not of the irradiation doses.

For chemotherapy, the effective dosage of the DNA-damaging antitumoral agent employed in the combined preparation, kit or product of the invention or in combination with the composition of the invention may vary depending on the particular DNA-damaging antitumoral agent employed, the mode of administration, the condition being treated, the severity of the condition being treated. Thus, the dosage regimen of the DNA-damaging antitumoral agent is selected in accordance with a variety of factors including the route of administration and the patient status. A physician, clinician or veterinarian of ordinary skill can readily determine and prescribe the effective amount of the DNA-damaging antitumoral agent required to prevent, counter or arrest the progress of the cancer.

The treatment may include one or several cycles, for instance two to ten cycles, in particular two, three, four or five cycles. The cycles may be continued or separated. For instance, each cycle is separated by a period of time of one to eight weeks, preferably three to four weeks.

Further aspects and advantages of the present invention will be described in the following examples, which should be regarded as illustrative and not limiting.

EXAMPLES

Example 1

In Vivo Test on Cell Survival

The inventors tested the effect of the combination of DT01 with either olaparib or veliparib on the survival of cells. More particularly, the results are shown in FIG. 1.

Breast cancer cell lines MDAMB231 were treated with 100 µg/ml (Black, Squares) or 333 µg/ml (Grey, Crosses) of DT01 or no DT01 (Black, Diamond) and exposed to either 0, 0.1 and 1 µM of Olaparib (upper panel) or 1, 10 and 50 µM Veliparib (lower panel). Survival was measured 6 days after treatment using trypan blue to detect living cells. The data are presented as % of the non-treated control. DT01 had a standalone effect resulting in 88% and 49% survival after exposure to 100 and 333 µg/ml. Adding PARP inhibitors, either Olaparib or Veliparib, increased significantly the cell death (full lines). The survival to combined treatment was inferior to the expected added effect of both single treatments (dotted lines), revealing a synergic effect at every tested dose of DT01 and PARP inhibitors.

Then, the combination of PARP inhibitors and Dbait molecules shows an antitumor effect higher than the expected addition of the effects of the single treatments. This supra-additivity is observed at every doses of each drug. The supra-additivity is observed with the combination of Dbait family with all the PARP inhibitors. Indeed, Olaparib belongs to the PARP inhibitors type (ii) whereas Veliparib belongs to the type (ii). Then the observed synergistic effect does not depend on the inhibiting mechanism.

Figure 2:
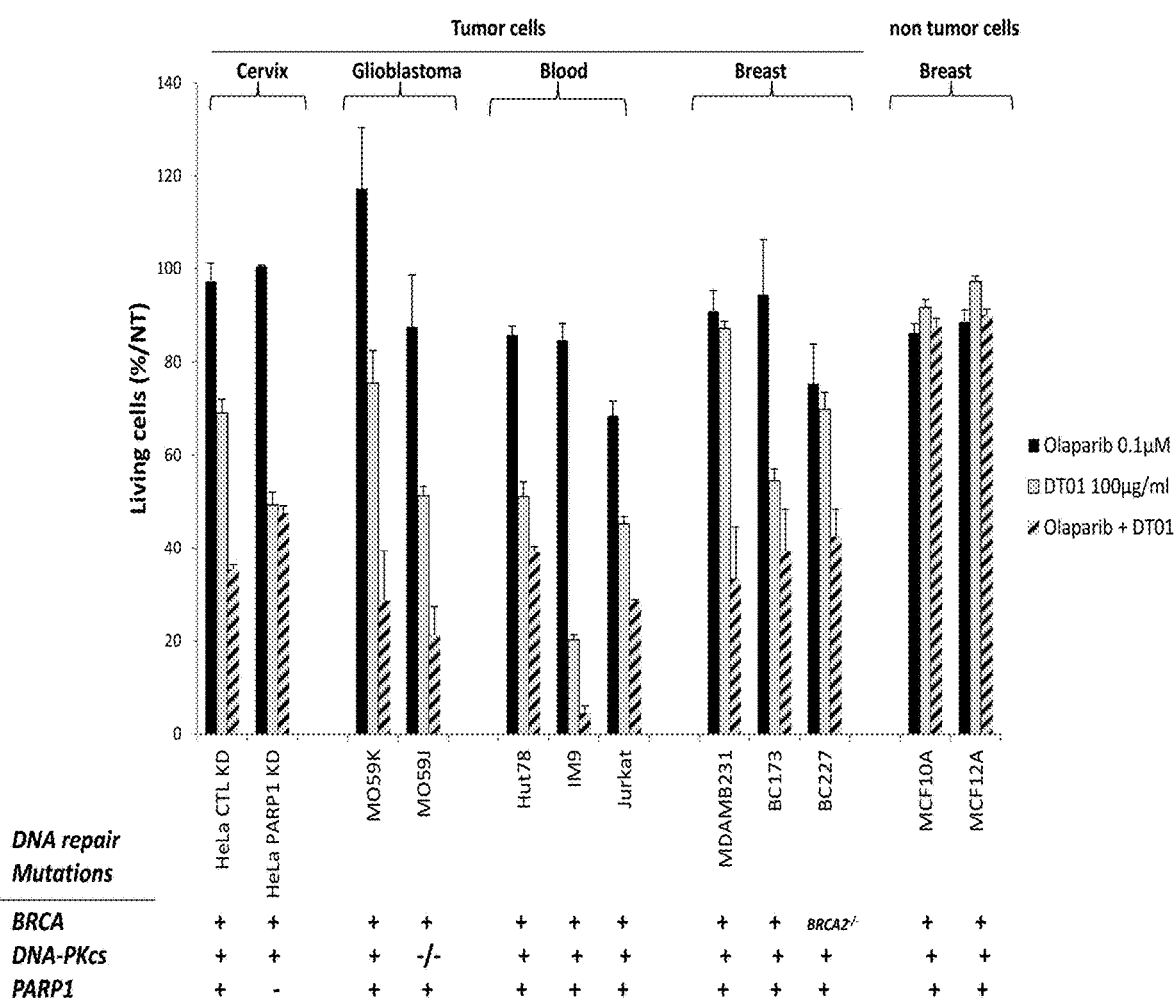
FIG. 2. The supra-additive effect of DT01 and Olaparib is not dependent of the cell line and DNA-PK or BRCA mutations. Survival of cells exposed to 0.1 µM Olaparib (black), 100 µg/ml DT01 (grey) or both treatments 0.1 µM Olaparib+ 100 µg/ml DT01 (hached) monitored in different tumor cells (from Cervix, Glioblastoma, Blood, Breast cancers) and two non tumoral breast cells.

The inventors tested the effect of the combination on several different cell lines. The results are shown in FIG. 2.

Survival of cells exposed to 0.1 µM Olaparib (black), 100 µg/ml DT01 (grey) or both treatments 0.1 µM Olaparib+ 100 µg/ml DT01 (hached) was monitored in different tumor cells (from Cervix, Glioblastoma, Blood, Breast cancers) and two non tumoral breast cells. The main mutations in DNA repair are indicated lower panel of the Figure.

The supra-additive effect of the combination was observed in all the cell lines whatever their defect in repair is (BRCA−/−, Homologous Recombination defect; DNA-PKcs−/−, Non Homologous End Joining defect). Only cells deficient in PARP activity (HelaPARP1KO) did not respond to the combination as they are insensitive to PARP inhibitors. Cancer cell lines known to be resistant to Olaparib such as Hela, MO59K, MO59J, Hut7, IM9, MD231, and BC173 show supra-additive effect of the combined treatment. Non-tumoral cells were insensitive to both single and combined treatments.

Materials and Methods

The human cell lines were grown in complete RPMI (Gibco, Cergy Pontoise, France) supplemented with 10% fetal bovine serum (ATGC, Orléans, France), 1% sodium pyruvate, streptomycin (100 mg·mL$^{-1}$) and penicillin (100 mg·mL$^{-1}$) (Invitrogen, Carlsbad, Calif., USA). Cells were maintained at 37° C. under a 5% CO$_2$ atmosphere, at 100% humidity. Treatments were performed by adding nucleotides (DT01 and others) or/and PARP inhibitors at time zero in medium without serum. The medium was changed with fresh medium containing fetal bovine serum 24 hours after beginning of treatment. Cells were let to grow for 4 additional days (5 days after treatment), treated with trypsin and counted for total number of cells. Trypan blue (0.4%) was added for counting the living cells (uncolored) in the population.

In Vivo Test on Tumor Growth

Figure 3:
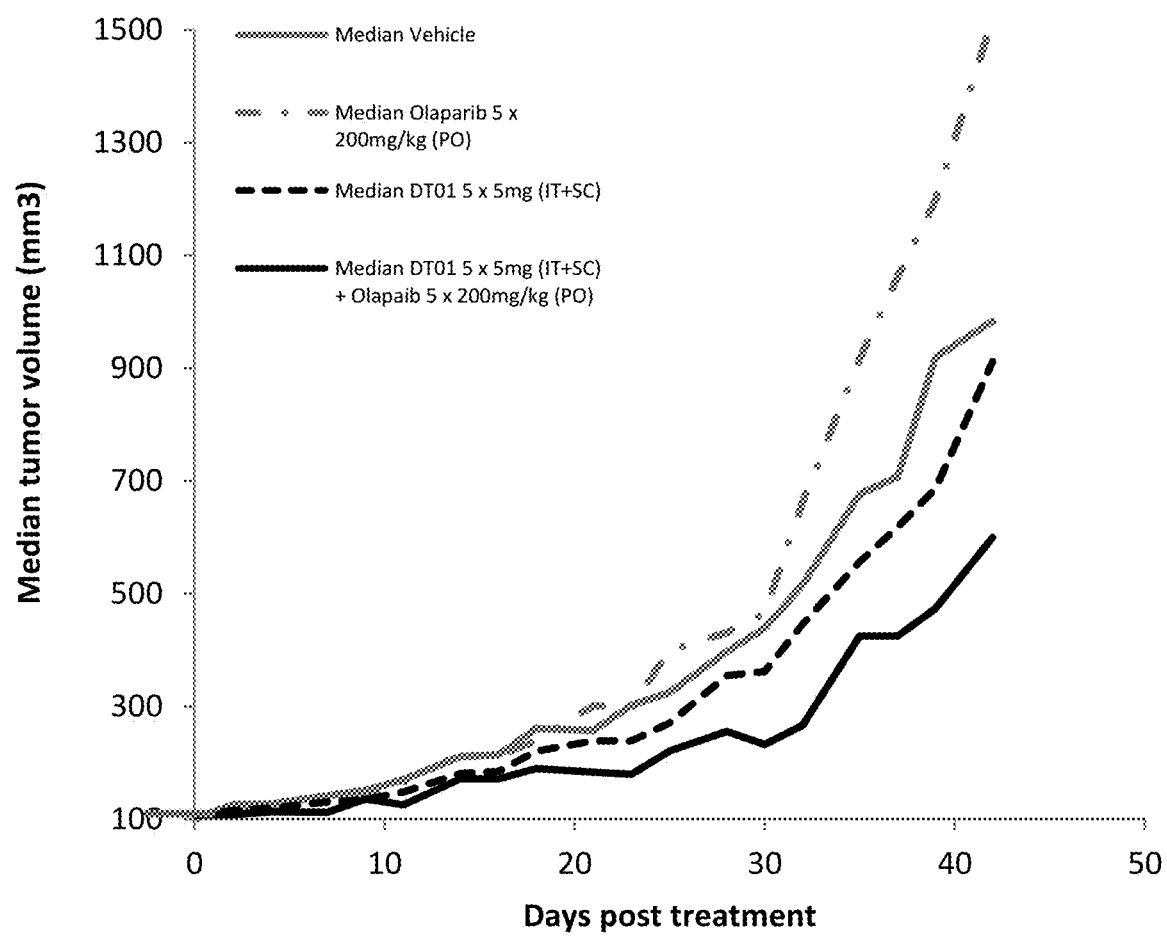
FIG. 3. In vivo synergy of DT01 and Olaparib.

Nude mice with xenografted MD227 human breast cancer cell lines grafted in the fat pad were treated by intratumoral administration of DT01 (5 mg/day) and Olaparib (200 mg/kg/day). Tumor growth was monitored (time zero: beginning of treatment). Eight to ten animals were treated per group (group 1: vehicle injection (grey line); group 2: DT01 (black dotted line); group 3: Olaparib (grey dotted line); group 4: DT01+ Olaparib (black line)). Treatment was administered 5 following days. The results are shown in FIG. 3 and demonstrate a decreased tumor size in comparison with animals treated with Olaparib alone or DT01 alone.

Materials and Methods

Human breast cancer xenograft tumors were obtained by injecting 4.10$^6$ tumor cells into the fat pad of adult female nude mice (Janvier, Le Genest Saint Isle, France). The animals were housed in the laboratory for at least 1 week before starting experiments. There were six animals per cage under controlled conditions of light and dark cycles (12 h: 12 h), relative humidity (55%), and temperature (21° C.). Food and tap water were available ad libitum. When subcutaneous tumors reached approximately 125 mm$^3$, mice were separated into homogeneous groups to receive different treatment protocols: no treatment (NT), DT01 alone for 1 week (2.5 mg intratumoral and 2.5 mg subcutaneous treatment every day for 5 days), Olaparib alone (200 mg/kg/day) for 1 week (5 daily sessions per os), and the combined treatment DT01+Olaparib 1 week (5 daily sessions. In all experiments, tumors were measured with a digital caliper every 2-3 days. No local skin toxicity or systemic toxicity was noted. Tumor volumes were calculated using the following formula: length×width×width/2. Mice were weighed every week and followed up for 280 days. For ethical reasons, the animals were sacrificed when tumors reached 1500 mm$^3$. The Local Committee on Ethics of Animal Experimentation approved all experiments.

Example 2

The inventors analyzed the combined effects of two classes of DNA repair inhibitors and demonstrate that their association mimics synthetic lethality in all cells. They compared the efficacy of a DBait (AsiDNA) and the PARP inhibitor (olaparib) in 12 Breast Cancer cell lines. Analysis of multi-level omics data from these cell lines, interpreted in the context of signaling network maps, highlighted different DNA repair molecular profiles associated with sensitivity to DBait or olaparib, rationalizing combined treatment. The supra-additive effect of the DBait and olaparib combined treatment was confirmed in 20 tumor cell lines with no significant cytotoxicity to non-tumor cells. Molecular analysis demonstrate that olaparib and DBait respectively prevent recruitment of XRCC1 and RAD51/53BP1 repair enzyme at damage sites and have cumulative effects when combined. Treatment synergy was also observed when combining DBait to other PARP inhibitors. The present results highlight the therapeutic interest of combining DBait and PARP inhibitors to recapitulate synthetic lethality in all tumors.

The inventors first analyzed the sensitivity to olaparib (Ola) and DBait in a panel of breast cancer (BC) cell lines. BC is the most common female malignancy, with more than 1.7 million new cases diagnosed each year worldwide. Inactivating mutations of BRCA are observed in 8.8% of all sporadic BC tumors with a prevalence of 30% in the Basal-like/Triple negative subgroup. They used a panel of BC cell lines with different BRCAness status, and first analyzed their sensitivity to the PARPi, olaparib (Ola) and DBait independently. BC cell lines were classified according to their sensitivity to DBait or Ola. Analysis of multi-level omics data from these cell lines in the context of comprehensive signaling network maps identified different molecular profiles associated to the sensitivity of DBait or Ola, especially in DNA repair mechanisms, highlighting the interest of combining these two drugs. The inventors observed a synergistic effect of Ola and DBait in the BC cell lines regardless of BRCAness status and demonstrate that this combination is effective in many cancer cell types and with different PARP inhibitors.

Results

BC Cell Lines Show Different Sensitivities to AsiDNA and Olaparib

Figure 4A:
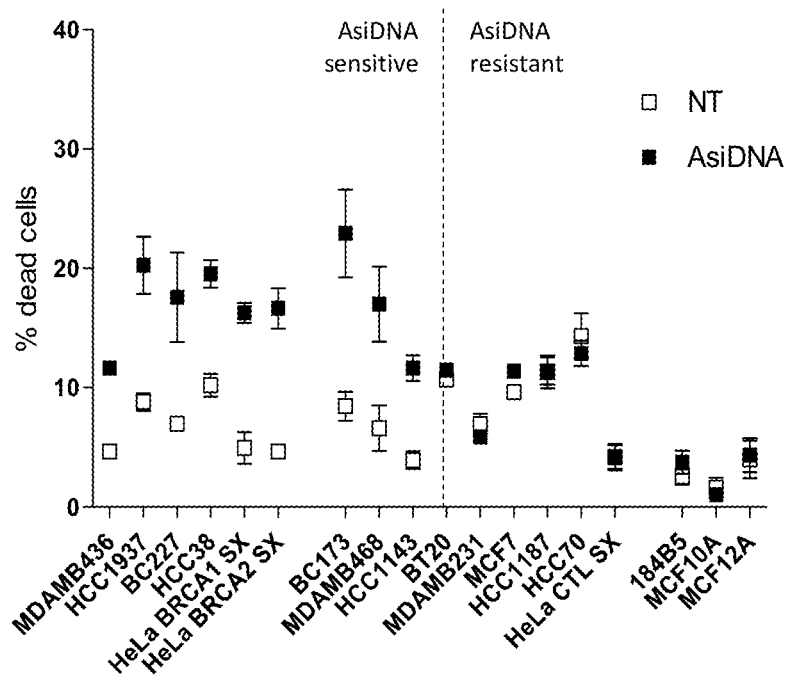
FIGS. 4A and 4B: Effect of the DNA repair inhibitors AsiDNA or Olaparib on cell death. Analysis of cell death in BC cell lines (MDAMB436, HCC1937, BC227, HCC38, BC173, MDAMB468, HCC1143, BT20, MDAMB231, HCC1187, and HCC70), cervix adenocarcinoma cell lines (HeLa CTL SX, HeLa BRCA1 SX and HeLa BRCA2 SX) and non-tumor mammary cell lines (184B5, MCF10 and MCF12A) treated with 4.8 µM AsiDNA (FIG. 4A) or 0.1 µM Ola (FIG. 4B). The dotted line indicates the sensitive cell lines for each treatment (defined by a mean difference in % dead cells higher than two-fold).
Figure 4B:
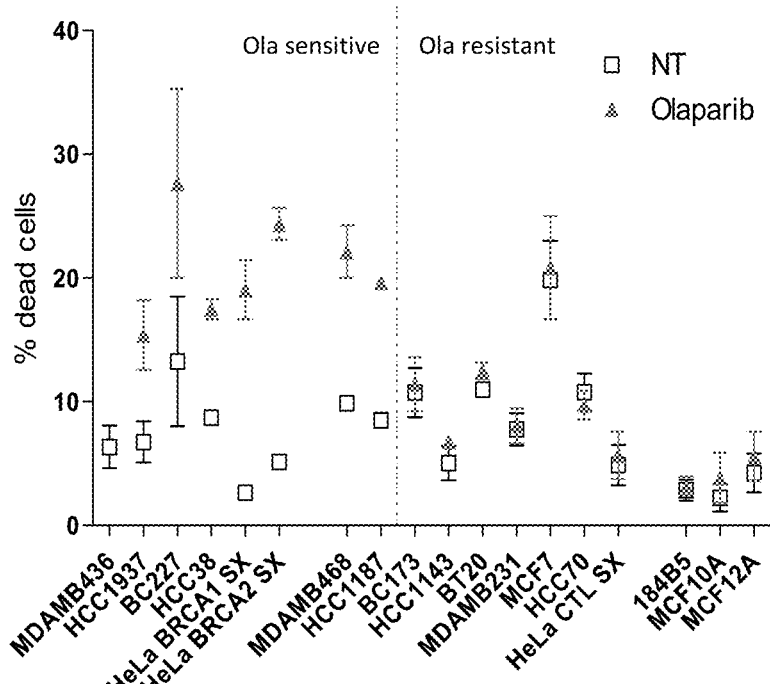
Figure 5:
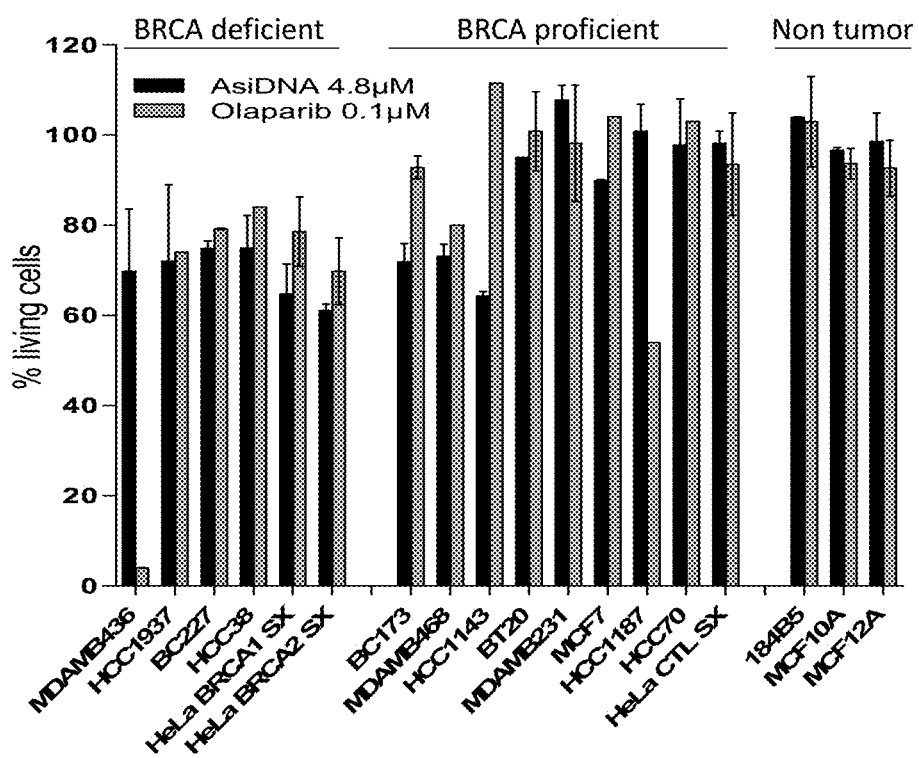
FIG. 5: Effect of the DNA repair inhibitors AsiDNA or Olaparib on cell survival. Analysis of cell survival in BC cell lines (MDAMB436, HCC1937, BC227, HCC38, BC173, MDAMB468, HCC1143, BT20, MDAMB231, HCC1187, HCC70), cervix adenocarcinoma cell lines (HeLa CTL SX, HeLa BRCA1 SX and HeLa BRCA2 SX) and non-tumor mammary cell lines (184B5, MCF10 and MCF12A) treated with 4.8 µM AsiDNA or 0.1 µM Ola. Survivals are expressed as % of living non-treated cells.

Efficacy of Ola and AsiDNA was assessed by measuring cell death and proliferation in 12BC cell lines including 4BRCA-mutated cell lines (FIGS. 4A and B and FIG. 5). In addition, HeLa cells silenced for BRCA1 or BRCA2 genes were used as a control of BRCA mutation factor and 3 immortalized mammary cell lines (MCF10A, MCF12A and 184B5) as non-tumor controls. The concentration of the drugs (0.1 µM for Ola and 4.8 µM for AsiDNA) were chosen based on the 75-80% survival in the BC227 BRCA2$^{-/-}$ mutant. In all BC cell lines, the decrease in the relative number of cells correlated with an increase in cell death (FIG. 4A, FIG. 5) indicating that the number of living cells reflects a cytotoxic and not a cytostatic effect. Ola and AsiDNA treatments had no effect on the three control non-tumor cell lines. In contrast, tumor cell lines revealed survival varying from 100% to 5% for Ola and 100% to 60% for AsiDNA. All the BRCA$^{-/-}$ cell lines were sensitive to both treatments. Among the BRCA proficient tumor cell lines, MDAMB468 was sensitive to both treatments, BC173 and HCC1143 were sensitive only to AsiDNA and HCC1187 was sensitive only to Ola. BT20, MDAMB231, MCF7 and HCC70 were resistant to both treatments at these doses (FIG. 4A, 4B and FIG. 5). Correlation analysis between response to AsiDNA and response to Ola revealed no significant correlation (Spearman coefficient r: 0.33 and P value: 0.17). These results indicate that BRCA deficiency is sufficient but not necessary for AsiDNA or Ola efficacy, and suggest that different repair defects determine sensitivity to these drugs.

Figure 6:
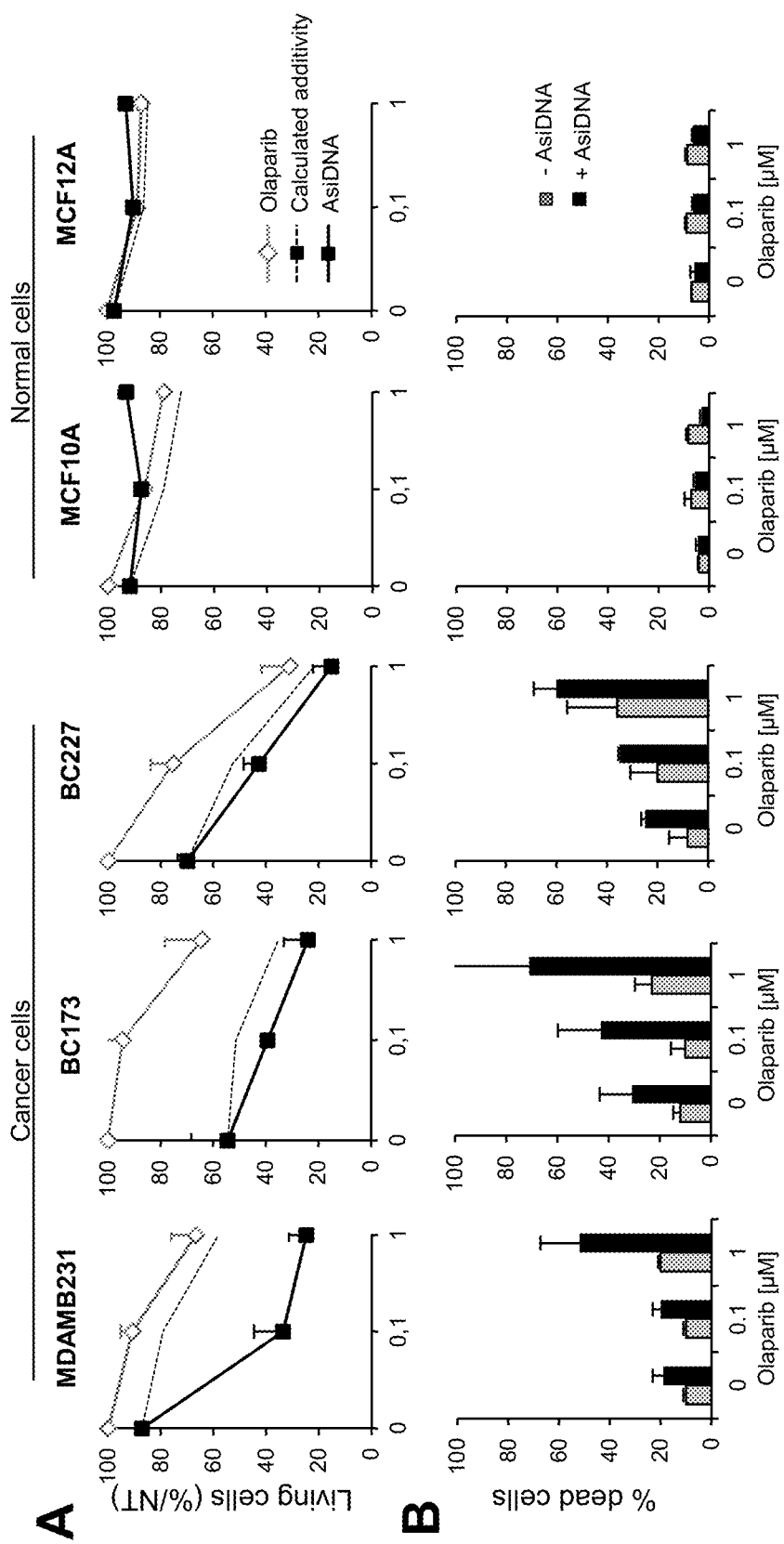
FIG. 6: Combined treatment displays a supra-additive efficacy. Efficacy of AsiDNA (4.8 µM), olaparib (0, 0.1 and 1 µM) or both was monitored 6 days after treatment by cell counting after trypan blue labeling. (A) Percentage of living cells relative to non-treated condition (NT). (B) Percentage of dead cells. Data are expressed as mean+Sc.D. of at least 2 independent experiments. Dotted lines indicate the calculated cell survivals if additivity between AsiDNA and olaparib.
Figure 7:
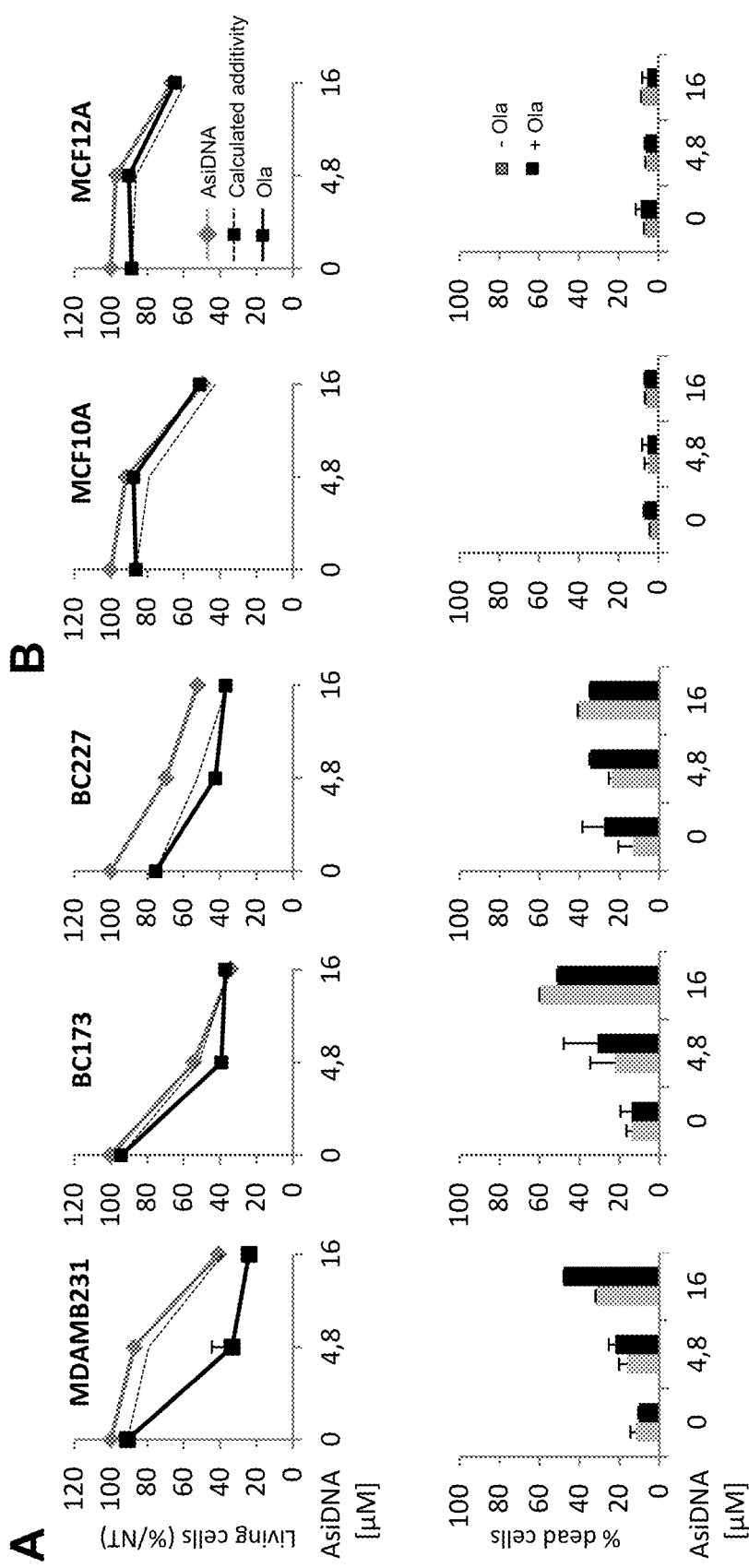
FIG. 7: Effect of the combined treatment AsiDNA and Olaparib. Analysis of cell survival (upper panel) and cell death (lower panel) in tumor (panel A) and non-tumor cell lines (panel B) in cultures treated with 0.1 µM Ola (black) or not (grey). Discontinuous lines indicate calculated cell survivals if additivity between AsiDNA and Ola (survival to AsiDNA x survival to Olaparib). Survivals and cell death were monitored by trypan blue staining and manual counting (6 days after treatment). Survivals are expressed as % of living non-treated cells and cell death as frequencies of dead cells.

Combined Treatment with AsiDNA and Olaparib Demonstrate Supra-Additive Efficacy in BC Cell Lines The inventors monitored cell survival to combined treatment of 3 BC and 2 non-tumor cell lines with different sensitivities to Ola and AsiDNA alone (FIG. 6; Table 1). Efficacy of Ola and AsiDNA single treatments was dose dependent (FIG. 7). However, the combination remained more efficient or at least equal to the expected additive effect at all the tested doses. Interestingly, the survival to combined treatment was supra-additive in the three cancer models regardless of the degree of sensitivity to the single treatments. Increasing the dose of AsiDNA to 16 µM had no significant effect on the combined treatment although it significantly increased the effect of AsiDNA single treatment. In contrast, the normal cells were insensitive to both, the combined and the single treatments with AsiDNA and Ola (FIG. 6; Table 1).

TABLE 1

Efficacy of the single and combined treatments in various cancer types.
Concentrations used were 4.8 µM of AsiDNA and 0.1 µM of Ola.
Calculated additivity = survival to AsiDNA × survival to Ola.

| | | DNA | Survival (%/NT) | | | |
|---|---|---|---|---|---|---|
| Cell line | Tissue | Repair defects | Ola | AsiDNA | AsiDNA + Ola | Calculated additivity |
| HeLa CTL KD | Cervix | — | 97.2 | 69.0 | 35.4 | 67.1 |
| HeLa PARP1 KD | | PARP1 | 100.5 | 49.3 | 47.6 | 49.5 |
| HeLa CTL SX | | — | 105.1 | 96.4 | 79.5 | 101.3 |
| HeLa BRCA1 SX | | BRCA1 | 71.4 | 64.6 | 27.9 | 46.2 |
| HeLa BRCA2 SX | | BRCA2 | 65.0 | 69.3 | 15.1 | 45.1 |
| Hep2 | Head and neck | — | 101 | 69.4 | 42.5 | 70 |
| MO59K | Brain | — | 117.3 | 75.4 | 28.7 | 88.5 |
| MO59J | | DNA-PKcs | 87.5 | 51.2 | 21.3 | 44.9 |
| SK28 Lsh CTL | Skin | — | 80.6 | 70.3 | 34.8 | 56.7 |
| SK28 Lsh DNA-PKcs | | DNA-PKcs | 80.9 | 50.8 | 33.6 | 41.1 |
| HCT116 | Colon | — | 82.9 | 80.0 | 36.6 | 66.3 |
| HCT116 KU70$^{+/-}$ | | KU70 | 88.6 | 77.3 | 42.3 | 68.5 |
| Hut78 | Blood | — | 85.8 | 51.1 | 39.1 | 43.8 |
| IM9 | | — | 84.6 | 20.3 | 4.6 | 17.1 |
| Jurkat | | — | 68.4 | 45.2 | 28.5 | 31.0 |
| MDAMB231 | Breast | — | 90.9 | 87.2 | 33.5 | 79.2 |
| BC173 | | — | 94.4 | 54.5 | 39.3 | 51.4 |
| BC227 | | BRCA2 | 75.3 | 69.8 | 42.6 | 52.6 |
| HCC38 | | BRCA1 | 66.7 | 69.5 | 25.7 | 46.3 |
| HCC1187 | | — | 61.5 | 103.8 | 41.5 | 63.9 |
| MDAMB468 | | — | 68.3 | 53.7 | 28.0 | 36.6 |
| MCF10A | Breast - non tumor | — | 86.2 | 91.7 | 87.5 | 79.0 |
| MCF12A | | — | 88.5 | 97.2 | 90.1 | 86.1 |

Molecular Mechanisms Underlying the Combination of AsiDNA and Olaparib

Figure 8:
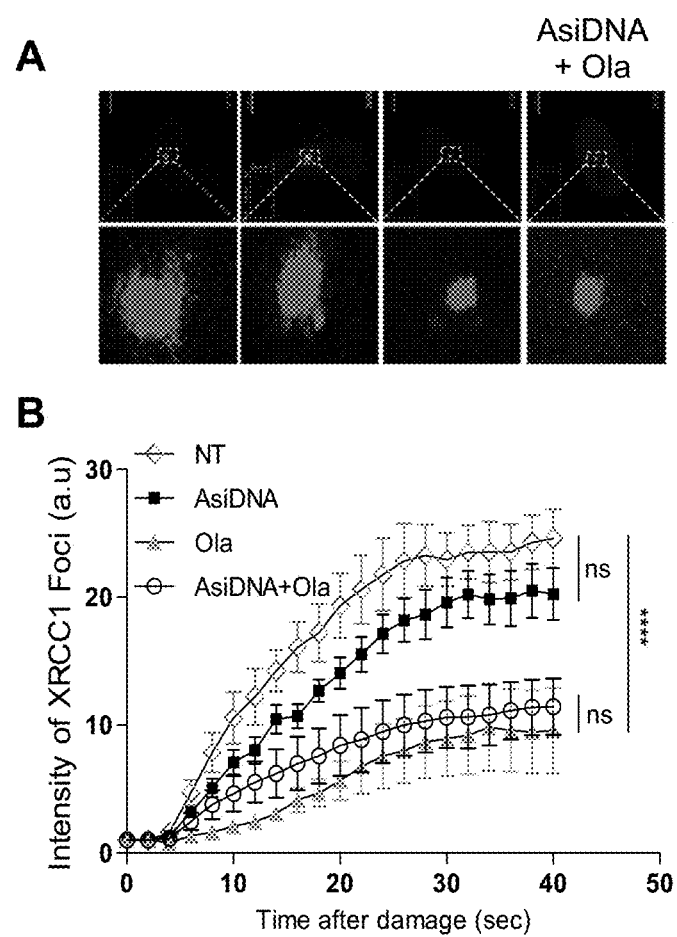
FIG. 8: Olaparib inhibits XRCC1 recruitment to damage sites independently of AsiDNA. (A) Representative images of XRCC1-eYFP recruitment 40 seconds after laser damage and (B) kinetic of XRCC1-eYFP recruitment in MDAMB231 cells after 24 h of treatment with Ola (1 µM) and/or AsiDNA (16 µM). ns: not significant; ****: p<0.0001. These experiments were performed with a Leica SP5 confocal system, attached to a DMI6000 stand using a 63/1.4 objective, under a controlled environment (37° C., 5% CO2). All records were made using the appropriate sampling frequency (512_512 images, line average of four and zooming set to eight) and an argon laser line (514 nm for YFP) adapted to the fluorescent protein of interest. In the first step, two images were acquired within a period of 2-3 s at a laser energy setting sufficiently low not to induce any photodynamic damage. The 405-nm laser line (diode) was then set to maximum output for 100 ms and focused onto a single spot of constant size (176 nm) within the nucleus to cause a point of photo damage with a reproducible amount of energy. Recruitment of the protein of interest was then monitored by fluorescence using the same setting as for the pre-damage sequence. Laser damage was induced 24 h after treatment with AsiDNA (16 µM), olaparib (1 µM) or both. Images were captured at 2 s intervals for the following 52 s.
Figure 9:
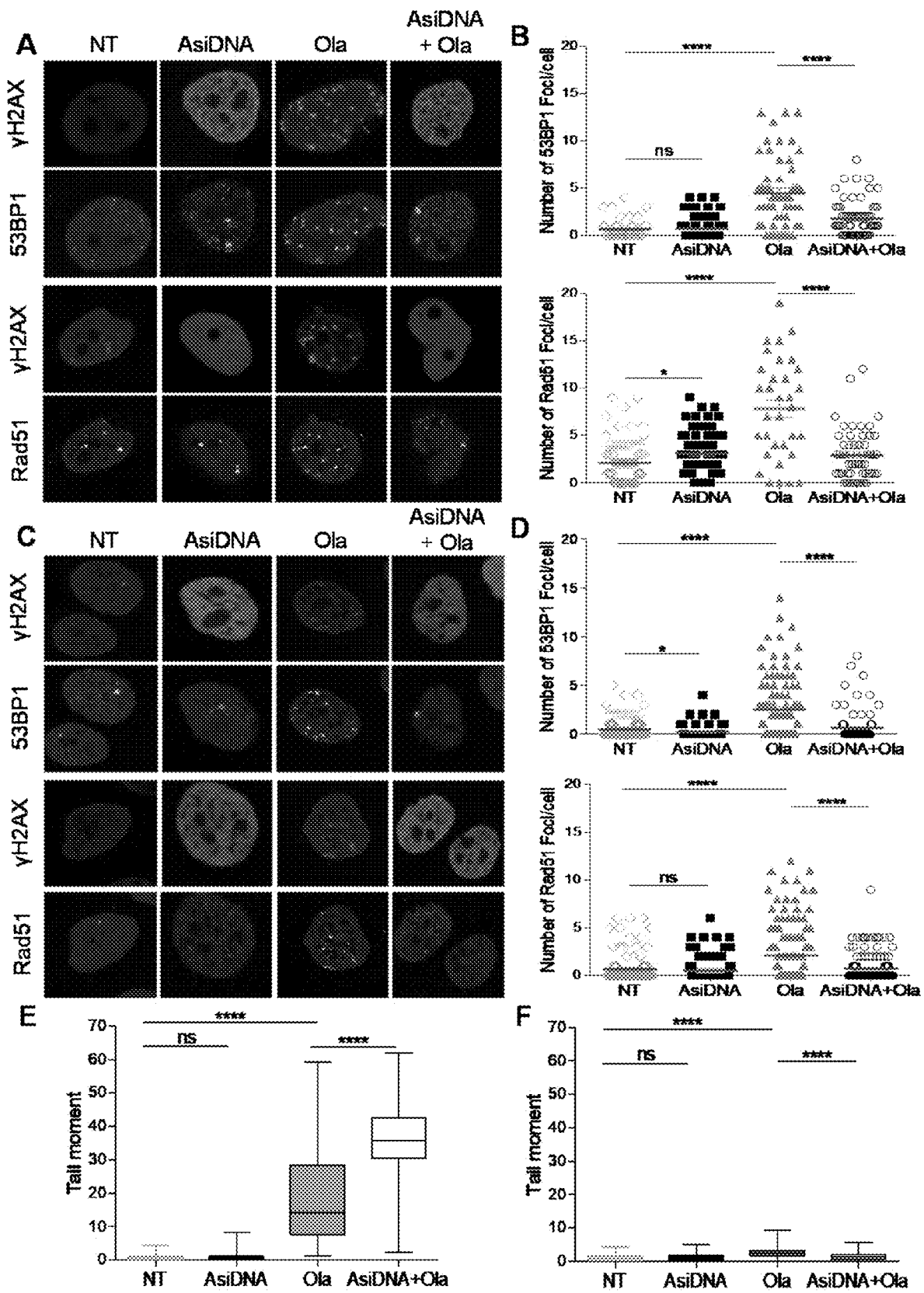
FIG. 9: Effect of the combined treatment AsiDNA and olaparib on DNA repair. Representative images of γH2AX (red) and Rad51 or 53BP1 (green) foci in MDAMB231 (A) or MCF10 (C) cells treated 24 h with Ola and/or AsiDNA. (B, D) Numbering of 53BP1 and Rad51 foci in 100 MDAMB231 cells (B) or MCF10A cells (D) 24 h after Ola and/or AsiDNA treatment. Red bars represent the mean values. (E, F) DNA damage monitored by alkaline comet assay 24 h after Ola and/or AsiDNA treatment in MDAMB231 (E) or MCF10A (F) cells. ns: not significant; *: p<0.05; ****: p<0.0001.
Figure 10:
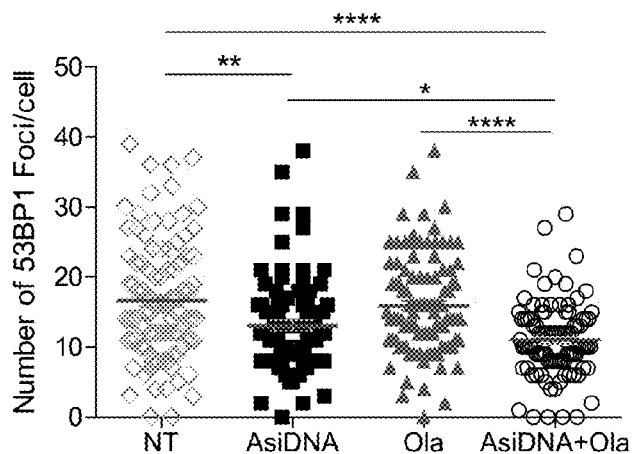
FIG. 10: AsiDNA inhibits irradiation-induced 53BP1 foci. Numbering of 53BP1 foci in 100 MDAMB231 cells 2 h after 10Gy irradiation, 22 h after prior treatment with AsiDNA and/or Ola. Red bars represent the mean values. *: $p<0.05$; : $p<0.01$; **: $p<0.0001$.

To dissect this cytotoxic synergy, the inventors examined the effect of AsiDNA, Ola or both on DNA repair activities. They first checked that each molecule does not affect the capacity of the other to inhibit recruitment of its targeted repair enzymes. As expected, Ola significantly delayed the XRCC1 foci recruitment while AsiDNA did not. The recruitment of XRCC1 was similarly delayed in cells treated with Ola in the presence and absence of AsiDNA (FIG. 8). Activation of DNA-PK kinase activity by AsiDNA can be easily revealed by the pan-nuclear phosphorylation of the histone H2AX. This phosphorylation was observed in the presence as in the absence of Ola (FIG. 9A, C). Pan-nuclear phosphorylation of H2AX is thought to be involved in the inhibition of HR and NHEJ repair enzyme recruitment by AsiDNA. After irradiation we observed a reduction of 53BP1 foci in the AsiDNA treated cells with and without Ola (FIG. 10). In the absence of DNA damaging treatment, Ola induces the accumulation of DSBs revealed by the formation of γH2AX foci that co-localize with 53BP1 and Rad51 foci (FIG. 9A, B). The addition of AsiDNA significantly reduced the formation of 53BP1 or Rad51 foci induced by Ola (FIG. 9A, B). To demonstrate that the reduction of Rad51 and 53BP1 foci after AsiDNA is induced by the inhibition of their recruitment at damage sites and not through a reduction of the number of DNA damage, the inventors used single cell alkaline comet assays to monitor the damage in MDAMB231 tumor cells after the different treatments. As suggested by γH2AX foci, Ola treatment induced accumulation of damage over 24 hours while AsiDNA did not (FIG. 9E). Combining AsiDNA to Ola resulted in a two-fold increase of DNA damage induced by Ola. This increase could account for the efficient toxicity of the combination in MDAMB231 cells. In contrast, in MCF10A non-tumor cells, even if a slight increase of DNA damage was observed after Ola treatment, combining AsiDNA to Ola did not increase damage accumulation (FIGS. 9C, D and F).

AsiDNA Increases Olaparib Efficacy in Other Cancer Cell Lines

Figure 11A:
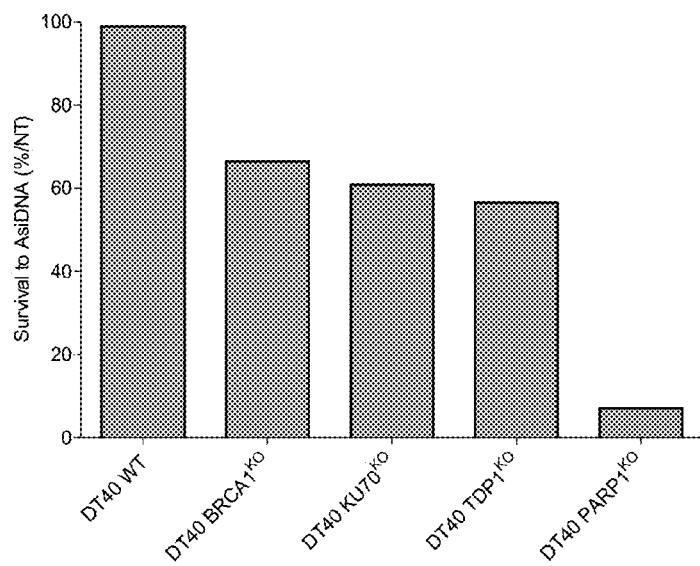
FIGS. 11A-11B: Synergy of AsiDNA and PARP defect.

To determine if the efficacy of the combination of AsiDNA with Ola was not restricted to BC, the inventors analyzed the sensitivity of different cancer cell lines including glioblastoma, cervical cancer, colon cancer, blood cancer and melanoma. All tumor models show supra-additive efficacy of the drug combination (Table 1). Moreover, analysis of isogenic pairs with DNA repair mutants to single and combined treatments indicates that AsiDNA is highly cytotoxic to all mutants with one repair defect (PARP1, BRCA1, BRCA2, Ku70, DNA-PKcs) whereas Ola sensitivity is essentially restricted to the BRCA mutants (Table 1). The sensitivity of PARP1, BRCA and Ku70 mutants to AsiDNA was confirmed in an isogenic set of DT40 chicken lymphoma repair mutants (FIG. 11A). The inventors also checked the effect of the combined treatment in three other BC cell lines (MDAMB468, HCC1187 and HCC38) that have different profiles of response to single treatments than MDAMB231, BC173 and BC227 (Table 1). Synergistic effect between AsiDNA and Ola was also observed in these three BC cell lines. Among cell lines derived from solid tumors, only HelaPARP1 silenced cells did not benefit from the combination as no increase of sensitivity to AsiDNA was observed after Ola treatment. Surprisingly, Hut78 and Jurkat blood tumor T cells had a survival to combined treatment close to the calculated additive effect of both single treatments (Table 1). Since both cell lines were sensitive to single treatments, the lack of additivity did not appear to correlate to specific DNA repair defects. Taken together, these results indicate that the efficiency of the combined treatment AsiDNA/Ola is not restricted to BC, and that AsiDNA sensitize all the cell lines to Ola independently of their BRCA status.

AsiDNA Leads to Supra-Additive Efficacy with all PARP Inhibitors

Figure 11B:
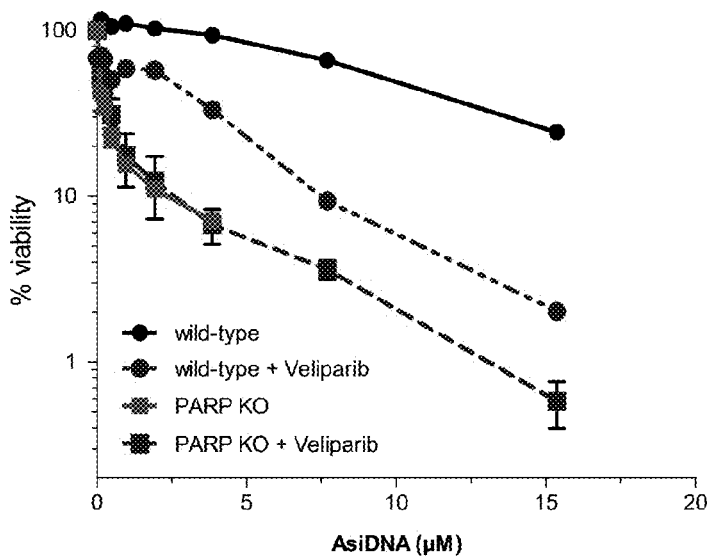
Figure 12:
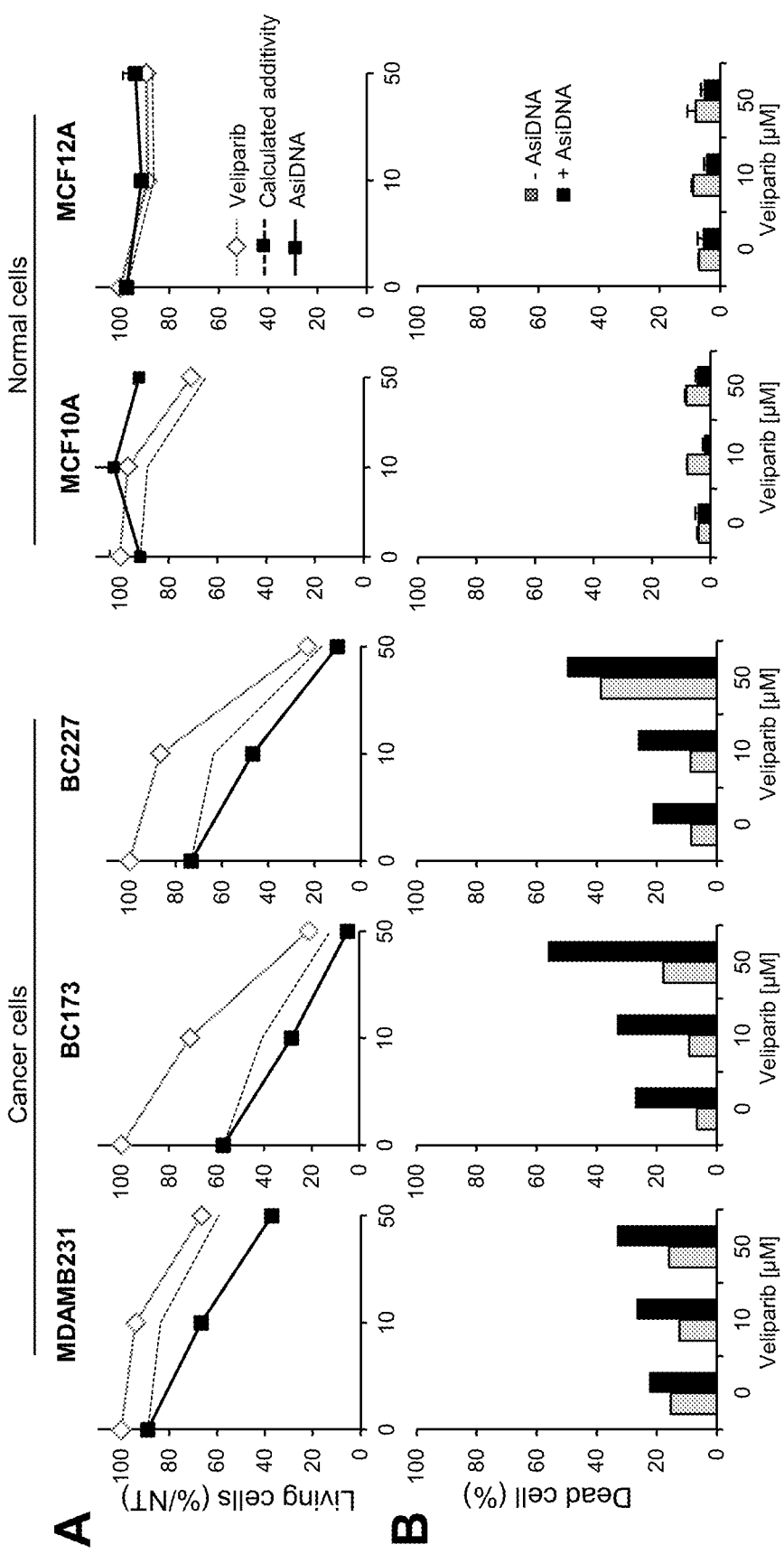
FIG. 12: AsiDNA association with veliparib displays a supra-additive efficacy. Efficacy of AsiDNA (4.8 µM), veliparib (0, 10 and 50 µM) or both was monitored 6 days after treatment by trypan blue staining. (A) Percentage of living cells relative to non-treated condition (NT). (B) Percentage of dead cells. Dotted lines indicate the calculated cell survivals if additivity between AsiDNA and veliparib.

PARP inhibitors belong to at least two classes: the catalytic inhibitors that inhibit PARP enzyme activity, and the dual inhibitors that block both PARP enzyme activity and trap PARP proteins on DNA damage sites. Ola belongs to the second group whereas veliparib (Veli) is only a catalytic inhibitor. Therefore the inventors repeated the analysis of efficacy in a panel of BC lines using Veli instead of Ola (FIG. 12). The synergistic effect of the combined treatment was observed with Veli in the three BC lines however this effect was absent in non-tumor cells. This indicates that trapping PARP on DNA is not essential for an efficient combination. Similar results were also observed in DT40 lymphoma cells (FIG. 11B).

Figure 13:
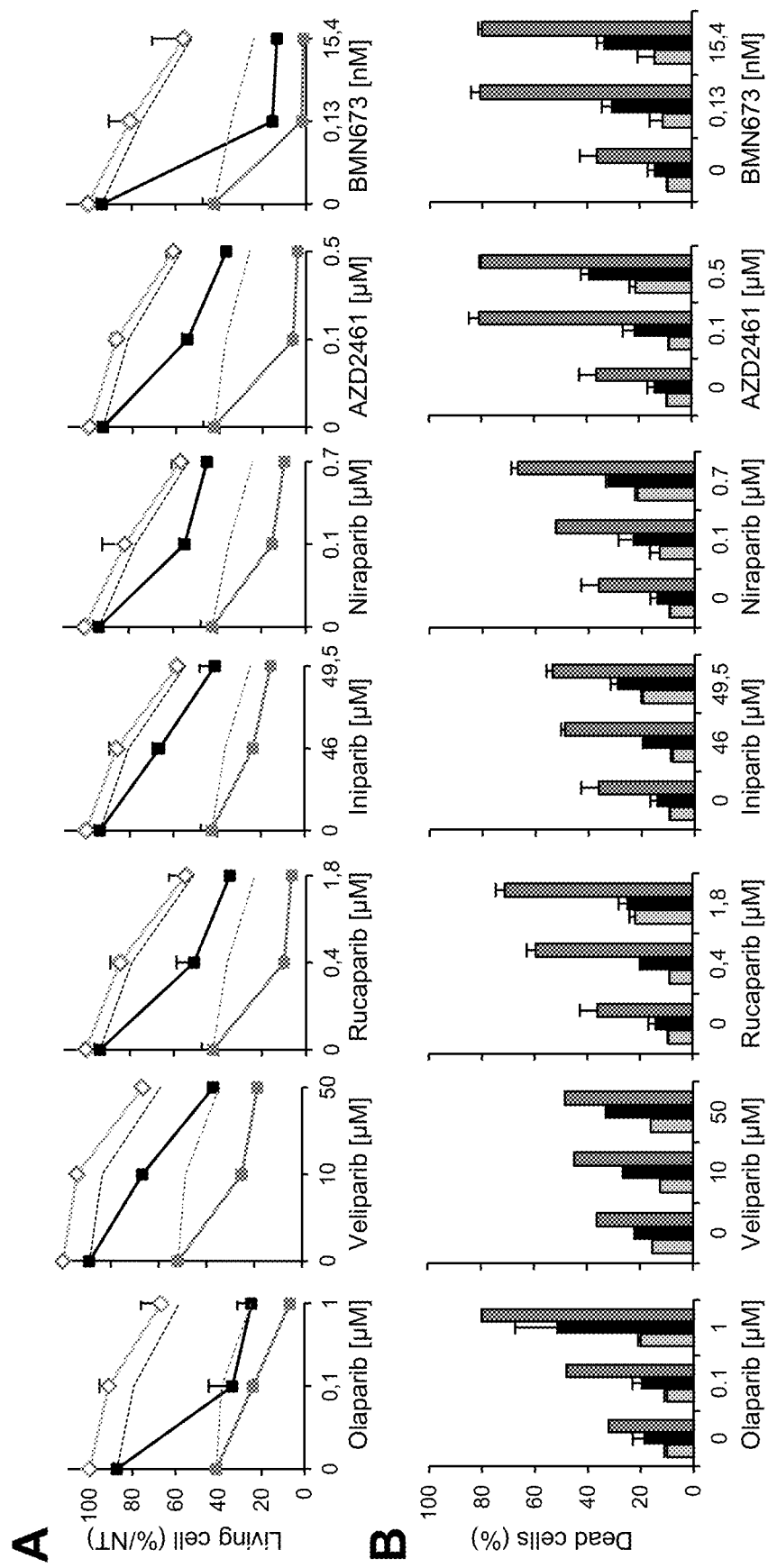
FIG. 13: Effect of the combined treatment AsiDNA and various PARPi on MDAMB231. Analysis of cell survival (A) and cell death (B) in MDAMB231 cell line in cultures treated with 4.8 µM AsiDNA (black), 16 µM AsiDNA (dark grey) or not (pale grey). Discontinuous lines indicate calculated cell survivals if additivity between AsiDNA and PARPi (survival to AsiDNA x survival to PARPi). Survivals and cell death were monitored 6 days after treatment. Survivals are expressed as % of living non-treated cells and cell death as frequencies of dead cells. PARPi doses were chosen to give 80% and 50% survival (table 2).

The inventors monitored the efficacy of the combined treatment in MDAMB231 cells with 5 other PARPi (rucaparib, iniparib, niraparib, AZD2461 and BMN673) developed for clinical applications (FIG. 13). The applied doses of PARPi were chosen to give a sub-lethal effect and a dose resulting in 50% survival (Table 2). The supra-additive efficacy of the combination of PARPi with AsiDNA was confirmed with all the inhibitors (FIG. 13) independently of their mechanism of action. These results demonstrate that the observed synergistic effects are general are not only restricted to olaparib.

TABLE 2

|  | IC20 (μM) | IC50 (μM) |
|---|---|---|
| Olaparib | 1 | 3.7 |
| Rucaparib | 0.4 | 1.8 |
| Iniparib | 46 | 49.5 |
| Niraparib | 0.1 | 0.7 |
| AZD2461 | 0.1 | 0.5 |
| BMN673 | 0.00013 | 0.0154 |

Materials and Methods
Cell Culture, Chemicals and AsiDNA Molecules

Cell cultures were performed with 4 BRCA1 deficient BC cells lines (BC227 from Institut Curie, HCC1937, HCC38 and MDAMB436 from ATCC), 8 BRCA1 proficient BC cell lines (BC173 from Institut Curie, BT20, HCC1143, HCC1187, HCC70, MCF7, MDAMB231 and MDAMB468 from ATCC), 3 non-tumor mammary cell lines (184B5, MCF10A and MCF12A from ATCC), 5 human cervical cancer HeLa cell lines silenced for BRCA1 (HelaBRCA1SX, Tebu-Bio referenced as 00301-00041), for BRCA2 (HelaBRCA2SX, Tebu-Bio referenced as 00301-00028), for PARP1 (HeLaPARP1KD, a kind gift of Vincent Pennanaech, Institut Curie, France) and controls (HeLaCTLSX, Tebu-Bio01-00001, and HeLaCTLKD a kind gift of Vincent Pennanaech, Institut Curie, France), human glioblastoma cell lines MO59K and MO59J (DNA-PKcs deficient), human melanoma cell lines SK28LshCTL and SK28 LshDNA-PKcs, human colorectal cancer cell lines HCT116 WT and HCT116 KU70$^{+/-}$ (heterozygote for KU70 gene), human head and neck cancer cell line Hep2, tumor blood cells Hut78, IM9 and Jurkat. Cells were grown according to the supplier's instructions. Cell lines were maintained at 37° C. in a humidified atmosphere at 5% $CO_2$.

DT40 Burkitt-lymphoma cells are chicken cells that have been knocked out for different genes as previously described in Murai et al (2012, Cancer Res, 72, 5588-99). For this study the inventors used DT40 wild type cells as control (DT40WT), and 4 cells lines respectively knocked out for BRCA1, KU70, TDP1 and PARP1 genes (DT40BRCA1KO, DT40KU70KO, DT40TDP1KO and DT40PARP1KO). The DT40 cells were cultured at 37° C. with 5% CO2 in Roswell Park Memorial Institute (RPMI-1640) medium supplemented with 1% chicken serum (Life Technologies, Carlsbad, Calif., USA), 10-5 M β-mercaptoethanol, penicillin, streptomycin and 10% fetal bovine serum (FBS). Reagents for cell cultivation were obtained from Gibco Invitrogen.

All PARP inhibitors, AZD-2281 (olaparib), AZD-2461, ABT888 (veliparib), MK-4827 (niraparib), BSI-201 (iniparib), BMN673 (talazoparib) and AG-014699 (rucaparib) were purchased from Medchem express (Princeton, USA) and diluted on DMSO to a stock concentration of 10 mM. DBait molecule (AsiDNA) are short double stranded 32 base pairs oligonucleotides made by automated solid-phase oligonucleotide synthesis methods (Agilent, USA). The sequence is: 5'XG̲C̲T̲GTGCCCACAACCCAGCAAACA-AGCCTAGA-L'-TCTAGGCTTGTTTGCTGGGTTG-TGGGCACA̲G̲C̲-3' (SEQ ID No 14) where L' is 1,19-bis (phospho)-8-hydraza-2-hydroxy-4-oxa-9-oxo-nonadecane and the letters underlined are phosphorodiamidate nucleosides. A cholesteryl tetraethyleneglycol (X) is linked at the 5' extremity.

Measurement of Cellular Sensitivity to Drugs

AsiDNA or PARPi cytotoxicity was measured by relative survival and cell death quantification. Adherent cells were seeded in 24-well culture plates at appropriate densities and incubated 24 hours at 37° C. before AsiDNA and/or PARPi addition. Cells were harvested day 6 after treatment, stained with 0.4% trypan blue (Sigma Aldrich, Saint-Louis, USA) and counted with a Burker chamber. Cell survival was calculated as ratio of living treated cells to living mock-treated cells. Cell death was calculated as the number of dead cells on the total number of counted cells. Additivity of the toxicity was calculated by the product of cell survivals to AsiDNA and cell survivals to PARPi.

To measure cytotoxicity in DT40 chicken lymphoma repair mutants (Murai et al, 2012, *Cancer Res,* 72, 5588-99), 750 cells were seeded in 96-well white plate (final volume 150 μl/well) from Perkin Elmer Life Sciences (Waltham, Mass., USA) in media with or without the indicated concentrations of the drugs (AsiDNA and/or veliparib) at 37° C. After 72 h, cells were assayed in triplicates with the ATPlite 1-step kit (PerkinElmer, Waltham, Mass., USA). Briefly, ATPlite solution was added to each well (150 μl for DT40 cells). After 5 minutes treatment, luminescence intensity was measured by Envision 2104 Multilabel Reader from Perkin Elmer Life Sciences (Waltham, Mass., USA). Signal intensities of untreated cells were set as 100%.

Antibodies and Immunological Studies

For immunostaining, MDAMB231 cells are seeded on cover slips (Menzel, Braunschweig, Germany) at a concentration of $5 \times 10^5$ cells and incubated at 37° C. during 1 day. Cells are then treated with 16 μM AsiDNA+/−1 μM olaparib. 24 h after treatment, cells are fixed for 20 min in 4% paraformaldehyde/Phosphate-Buffered Saline (PBS 1×), permeabilized in 0.5% Triton X-100 for 10 min, blocked with 2% bovine serum albumin/PBS 1× and incubated with primary antibody for 1 h at 4° C. All secondary antibodies were used at a dilution of 1/200 for 45 min at Room Temperature (RT), and DNA was stained with 4', 6-diamidino-2-phenylindole (DAPI). The following antibodies were used: primary monoclonal mouse anti-phospho-H2AX (Millipore, Guyancourt, France), anti-53BP1 rabbit antibody (Cell signaling technology, Danvers, USA), anti-Rad51 rabbit antibody (Merk Millipore, Darmstadt, Allemagne), secondary goat anti-mouse IgG conjugated with Alexa-633 (Molecular Probes, Eugene, Oreg., USA) and secondary goat anti-rabbit IgG conjugated with Alexa-488 (Molecular Probes, Eugene, Oreg., USA).

Alkaline Single-Cell Electrophoresis "COMET Assay"

Cells treated with AsiDNA (16 μM), olaparib (1 μM) or both were suspended in 0.5% low melting point agarose in DMEM and transferred onto a frosted glass microscope slide precoated with a layer of 0.5% normal melting point agarose. Slides were immersed in lysis solution [2.5 mol/L NaCl, 100 mmol/L EDTA, 10 mmol/L Tris, 1% sodium lauryl sarcosinate, 10% DMSO, 1% Triton X-100 (pH 10)] at 4jC for 1 h, placed in a electrophoresis tank containing 0.3 mol/L NaOH (pH 13) and 1 mmol/L EDTA for 40 min, electrophoresis for 25 min at 25 V (300 mA), washed with neutral buffer [400 mmol/L Tris-HCl (pH 7.5)], and stained with 20 Ag/mL ethidium bromide. The variables of the "comets" were quantified with the use of the software Comet Assay 2 (Perceptive Instrument). Triplicate slides were processed for each experimental point. The tail moment is defined as the product of the percentage of DNA in the tail and the displacement between the head and the tail of the comet.

Statistical Analysis

All statistical analysis was performed with a two-tailed Student's t-test.

We claim:

1. A pharmaceutical composition comprising a nucleic acid molecule and a poly(ADP-ribose)polymerase (PARP) inhibitor, wherein the nucleic acid molecule is a hairpin nucleic acid with a double-stranded DNA stem and a loop and has the following formula:

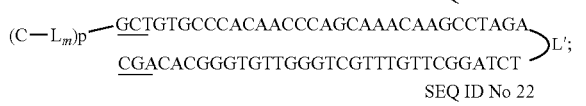

(IId)

SEQ ID No 14

SEQ ID No 22 wherein C is a cholesteryl, Lm is a carboxamido tetra-ethylene glycol linker, p is 1 and L' is 1,19-bis(phospho)-8-hydraza-2-hydroxy-4-oxa-9-oxo-nonadecane.

2. The pharmaceutical composition according to claim 1, wherein the nucleic acid molecule is:

consisting of rucaparib (AG014699, PF-01367338), olaparib (AZD2281), veliparib (ABT888), iniparib (BSI 201), niraparib (MK 4827), talazoparib (BMN673), AZD 2461, CEP 9722, E7016, INO-1001, LT-673, MP-124, NMS-P118, XAV939, analogs, derivatives or a mixture thereof.

4. The pharmaceutical composition according to claim 1, wherein the PARP inhibitor is selected from the group consisting of AZD2281 (Olaparib), ABT888 (Veliparib), BMN673, BSI-21 (Iniparib), AZD 2461, MK-4827 (Niraparib), and AG 014699 (Rucaparib).

5. A method of treating cancer which is not deficient or impaired for the homologous recombination repair, comprising the administration of the pharmaceutical composition according to claim 1 to a subject in need thereof.

6. The method according to claim 5, wherein the cancer is selected from leukemia, lymphoma, sarcoma, melanoma, and cancers of the head and neck, kidney, ovary, pancreas, prostate, thyroid, lung, esophagus, breast, bladder, brain, colorectum, liver, and cervix.

7. The method according to claim 5, wherein the PARP inhibitor is used at a sub-therapeutic amount.

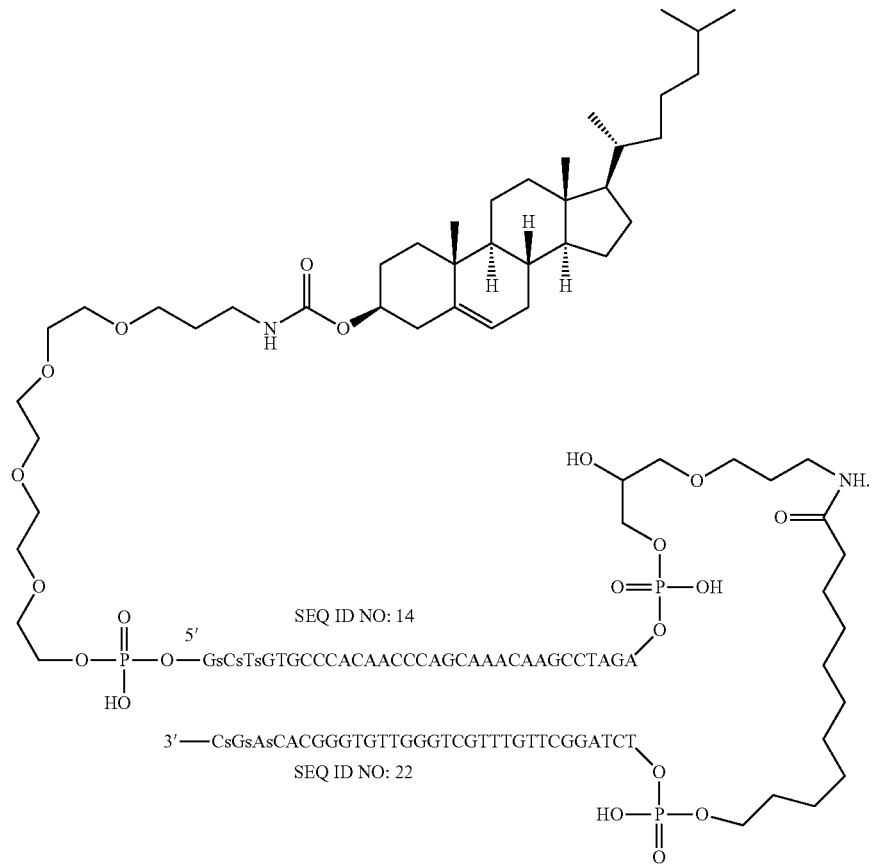

3. The pharmaceutical composition according to claim 1, wherein the PARP inhibitor is selected from the group 8. The method according to claim 5, wherein the PARP inhibitor and the DBait nucleic acid molecule are used in combination with radiotherapy and/or an antitumor chemotherapy with a DNA damaging agent.

9. A kit comprising a PARP inhibitor and a nucleic acid molecule, wherein the nucleic acid molecule is a hairpin nucleic acid with a double-stranded DNA stem and a loop and has the following formula:

II(d)

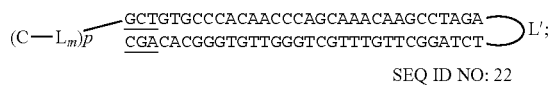

SEQ ID NO: 14

SEQ ID NO: 22 wherein C is a cholesteryl, Lm is a carboxamido tetraethylene glycol linker, p is 1 and L' is 1,19-bis(phospho)-8-hydraza-2-hydroxy-4-oxa-9-oxo-nonadecane.

10. The kit according to claim 9, wherein the nucleic acid molecule is:

zoparib (BMN673), AZD 2461, CEP 9722, E7016, INO-1001, LT-673, MP-124, NMS-P118, XAV939, analogs, derivatives or a mixture thereof.

13. The kit according to claim 9, wherein the PARP inhibitor is selected from the group consisting of AZD2281 (Olaparib), ABT888 (Veliparib), BMN673, BSI-21 (Iniparib), AZD 2461, MK-4827 (Niraparib), and AG 014699 (Rucaparib).

14. The kit according to claim 10, wherein the PARP inhibitor is selected from the group consisting of AZD2281 (Olaparib), ABT888 (Veliparib), BMN673, BSI-21 (Iniparib), AZD 2461, MK-4827 (Niraparib), and AG 014699 (Rucaparib).

15. The pharmaceutical composition according to claim 2, wherein the PARP inhibitor is selected from the group

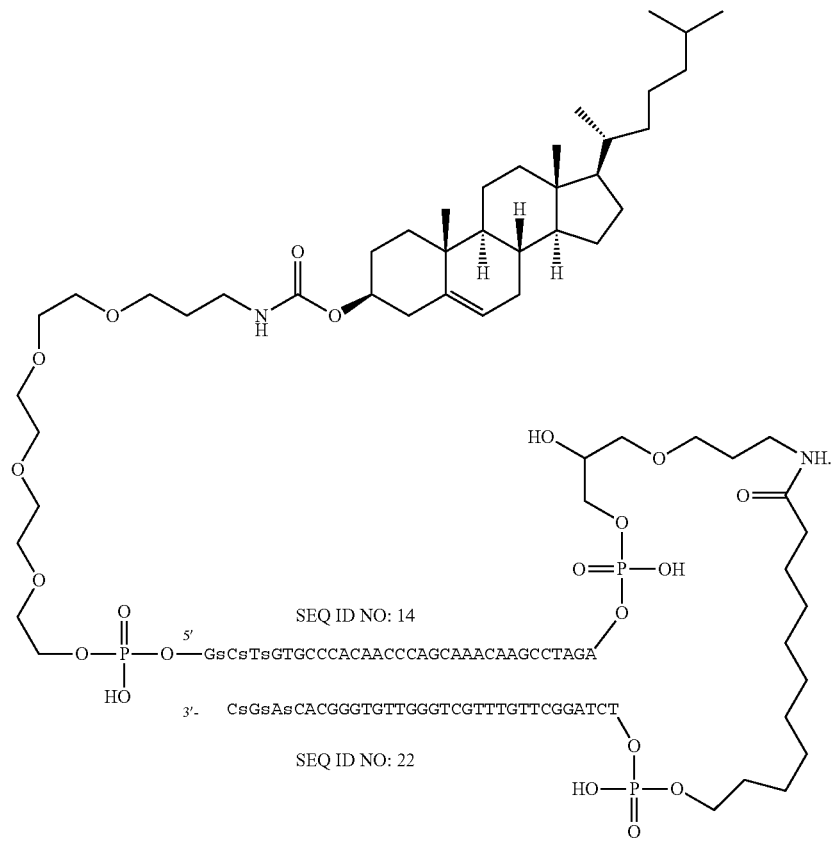

11. The kit according to claim 9, wherein the PARP inhibitor is selected from the group consisting of rucaparib (AG014699, PF-01367338), olaparib (AZD2281), veliparib (ABT888), iniparib (BSI 201), niraparib (MK 4827), talazoparib (BMN673), AZD 2461, CEP 9722, E7016, INO-1001, LT-673, MP-124, NMS-P118, XAV939, analogs, derivatives or a mixture thereof.

12. The kit according to claim 10, wherein the PARP inhibitor is selected from the group consisting of rucaparib (AG014699, PF-01367338), olaparib (AZD2281), veliparib (ABT888), iniparib (BSI 201), niraparib (MK 4827), talazoparib (BMN673), AZD 2461, CEP 9722, E7016, INO-1001, LT-673, MP-124, NMS-P118, XAV939, analogs, derivatives or a mixture thereof.

16. The pharmaceutical composition according to claim 2, wherein the PARP inhibitor is selected from the group consisting of AZD2281 (Olaparib), ABT888 (Veliparib), BMN673, BSI-21 (Iniparib), AZD 2461, MK-4827 (Niraparib), and AG 014699 (Rucaparib).

* * * * *

UNITED STATES PATENT AND TRADEMARK OFFICE
CERTIFICATE OF CORRECTION

PATENT NO. : 11,162,095 B2
APPLICATION NO. : 16/790788
DATED : November 2, 2021
INVENTOR(S) : Marie Dutreix and Wael Jdey Page 1 of 2

It is certified that error appears in the above-identified patent and that said Letters Patent is hereby corrected as shown below:

In the Specification

Column 5,
Line 17, "(AGO 14699," should read --(AG014699,--.

Column 24,

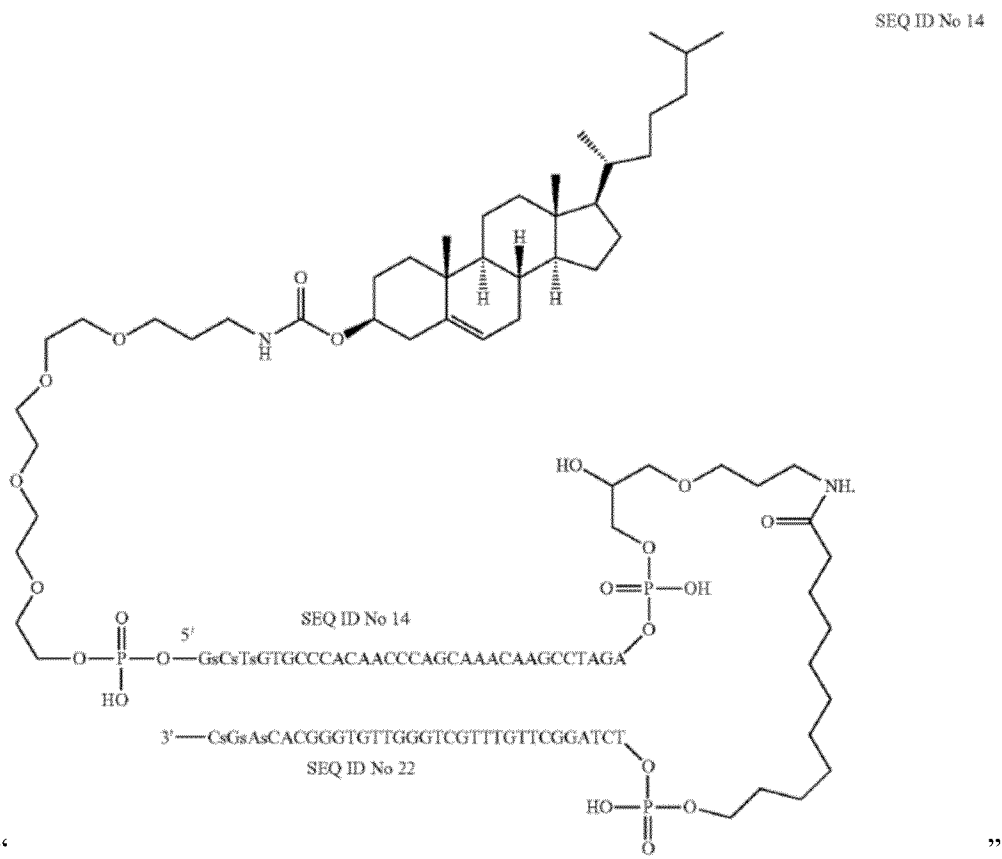

Lines 33-67, " "

Signed and Sealed this
Twelfth Day of April, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,162,095 B2

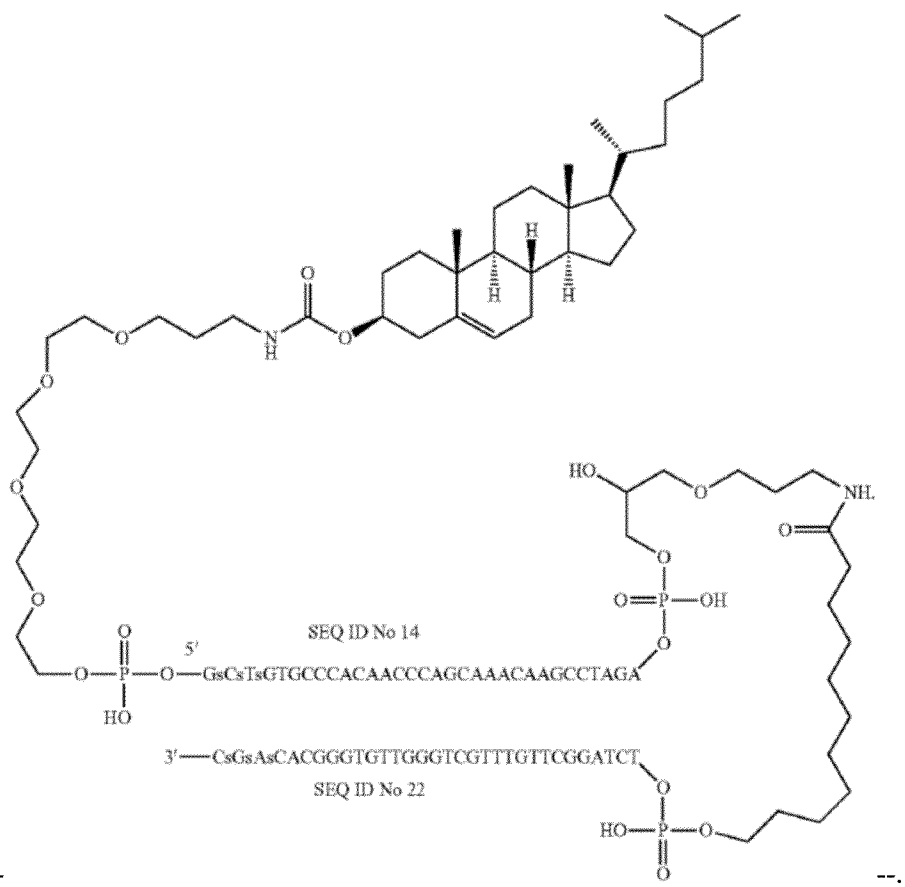

should read --

Column 26,
Line 19, "Silver-ill" should read --Silver-111--.

Column 37,
Line 21, "53BP land" should read --53BP1 and--.